United States Patent

Culshaw et al.

(10) Patent No.: US 7,732,435 B2
(45) Date of Patent: Jun. 8, 2010

(54) CHROMONE DERIVATIVES USEFUL AS ANTAGONISTS OF VR1 RECEPTORS

(75) Inventors: Andrew James Culshaw, Horsham (GB); Christopher Thomas Brain, Cambridge, MA (US); Edward Karol Dziadulewicz, Frimley (GB); Lee Edwards, Horsham (GB); Terance William Hart, High Peak (GB); Timothy John Ritchie, Stevenage (GB)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 12/096,244

(22) PCT Filed: Dec. 5, 2006

(86) PCT No.: PCT/EP2006/069303

§ 371 (c)(1),
(2), (4) Date: Jun. 5, 2008

(87) PCT Pub. No.: WO2007/065888

PCT Pub. Date: Jun. 14, 2007

(65) Prior Publication Data

US 2008/0312316 A1 Dec. 18, 2008

(30) Foreign Application Priority Data

Dec. 5, 2005 (GB) .................... 0524808.3

(51) Int. Cl.
| | |
|---|---|
| A61K 31/5365 | (2006.01) |
| A61K 31/424 | (2006.01) |
| A61K 31/553 | (2006.01) |
| A61K 31/407 | (2006.01) |
| A61K 31/4162 | (2006.01) |
| A61K 31/4192 | (2006.01) |
| A61K 31/551 | (2006.01) |
| C07D 265/36 | (2006.01) |
| C07D 498/14 | (2006.01) |
| C07D 497/14 | (2006.01) |
| C07D 487/14 | (2006.01) |
| C07D 491/153 | (2006.01) |

(52) U.S. Cl. .................. 514/211.1; 514/220; 514/229.8; 514/359; 514/375; 514/394; 514/406; 514/411; 540/488; 540/557; 544/101; 548/218; 548/256; 548/302.1; 548/359.5; 548/430

(58) Field of Classification Search ....................... None
See application file for complete search history.

(56) References Cited

U.S. PATENT DOCUMENTS 4,419,352 A 12/1983 Cox et al.

FOREIGN PATENT DOCUMENTS

| WO | 2005121116 A | 12/2005 |
| WO | WO 2005/121116 | * 12/2005 |

OTHER PUBLICATIONS

Edwards, J M, et al: "Antineoplastic activity and cytotoxicity of flavones, isoflavones, and flavanones" Journal of natural products, vol. 42, No. 1, 1979, pp. 85-91. p. 90; table 2.

* cited by examiner

Primary Examiner—Golam M. M. Shameem
Assistant Examiner—Alicia L Fierro

(57) ABSTRACT

The invention relates to novel heterocyclic compounds of the formula

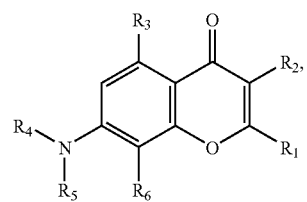

(I)

in which all of the variables are as defined in the specification, in free form or in salt form, to their preparation, to their use as medicaments and to medicaments comprising them.

4 Claims, No Drawings

CHROMONE DERIVATIVES USEFUL AS ANTAGONISTS OF VR1 RECEPTORS

This application is the National Stage of Application No. PCT/EP2006/069303, filed on Dec. 5, 2006, which claims benefit under 35 U.S.C. §119(a)-(d) or (f) or 365(b) of GB Application No. 0524808.3, filed Dec. 5, 2005, the contents of which are incorporated herein by reference in their entirety.

The present invention relates to novel heterocyclic compounds, to their preparation, to their use as pharmaceuticals and to pharmaceutical compositions comprising them.

More particularly, the invention relates to a compound of the formula

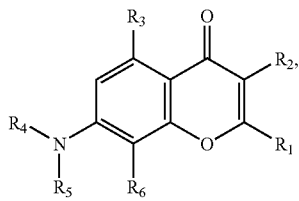

in which $R_1$ is halogen, $C_1$-$C_8$alkyl, halo-$C_1$-$C_6$alkyl, $C_1$-$C_6$alkoxy-$C_1$-$C_6$alkyl, $C_3$-$C_6$cycloalkyl, $C_3$-$C_6$cycloalkyl-$C_1$-$C_6$alkyl, $C_1$-$C_6$alkylamino, pyrrolidinyl, tetrahydrofuryl or tetrahydrothienyl;

$R_2$ is an aryl or heteroaryl group, which is optionally substituted by 1, 2 or 3 substituents, selected from the group consisting of halogen, $C_1$-$C_6$alkyl, halo-$C_1$-$C_6$alkyl, hydroxy, hydroxy-$C_1$-$C_6$alkyl, $C_1$-$C_6$alkoxy, $C_1$-$C_6$alkoxy-$C_1$-$C_6$alkyl, halo-$C_1$-$C_6$alkoxy, $C_1$-$C_6$alkylthio, halo-$C_1$-$C_6$alkylthio, $C_1$-$C_6$alkylsulfinyl, halo-$C_1$-$C_6$alkylsulfinyl, $C_1$-$C_6$alkylsulfonyl, halo-$C_1$-$C_6$alkylsulfonyl, $C_3$-$C_6$cycloalkyl, $C_3$-$C_6$cycloalkyl-$C_1$-$C_6$alkyl, $C_3$-$C_6$cycloalkoxy, $C_3$-$C_6$cycloalkoxy-$C_1$-$C_6$alkyl, amino, $C_1$-$C_6$alkylamino, di-($C_1$-$C_6$alkyl)amino, $C_1$-$C_6$alkoxycarbonylamino, cyano, formyl and $C_1$-$C_6$alkylcarbonyl, or which is substituted at two adjacent carbon atoms by —O—CH$_2$—O— or —O—CF$_2$—O—;

$R_3$ is hydrogen, hydroxy or $C_1$-$C_6$alkoxy;

$R_4$ is hydrogen, formyl, $C_1$-$C_6$alkylcarbonyl or benzyl, the phenyl group of which is optionally substituted by 1, 2 or 3 substituents, selected from the group consisting of halogen, $C_1$-$C_6$alkyl, halo-$C_1$-$C_6$alkyl, hydroxy, hydroxy-$C_1$-$C_6$alkyl, $C_1$-$C_6$alkoxy, $C_1$-$C_6$alkoxy-$C_1$-$C_6$alkyl, halo-$C_1$-$C_6$alkoxy, $C_1$-$C_6$alkylthio, halo-$C_1$-$C_6$alkylthio, $C_1$-$C_6$alkylsulfinyl, halo-$C_1$-$C_6$alkylsulfinyl, $C_1$-$C_6$alkylsulfonyl, halo-$C_1$-$C_6$alkylsulfonyl, $C_3$-$C_6$cycloalkyl, $C_3$-$C_6$cycloalkyl-$C_1$-$C_6$alkyl, $C_3$-$C_6$cycloalkoxy, $C_3$-$C_6$cycloalkoxy-$C_1$-$C_6$alkyl, amino, $C_1$-$C_6$alkylamino, di-($C_1$-$C_6$alkyl)amino, $C_1$-$C_6$alkoxycarbonylamino, cyano, formyl and $C_1$-$C_6$alkylcarbonyl, or is substituted at two adjacent carbon atoms by —O—CH$_2$—O— or —O—CF$_2$—O—; and $R_5$ and $R_6$, taken together, represent, together with the three-membered moiety —N—C—C—, to which they are attached, a five-, six-, seven- or eight-membered, partially or fully unsaturated, optionally substituted, heterocyclic ring, which contains 1 ring nitrogen atom and optionally either 1 further ring nitrogen, oxygen or sulfur atom or 2 further ring nitrogen atoms, in which heterocyclic ring each ring oxygen or sulfur atom is bonded to 2 ring carbon atoms, the optional substituents of the said heterocyclic ring being selected from the group consisting of halogen, $C_1$-$C_6$alkyl, halo-$C_1$-$C_6$alkyl, hydroxy-$C_1$-$C_6$alkyl and oxo, in free form or in salt form.

If at least one asymmetrical carbon atom is present in a compound of the formula I, such a compound may exist in optically active form or in the form of mixtures of optical isomers, e. g. in the form of racemic mixtures. All optical isomers and their mixtures, including the racemic mixtures, are part of the present invention.

Halogen (or halo) denotes fluorine, bromine, chlorine or iodine.

Aryl is naphthyl or preferably phenyl. It can also be fused with a cycloalkyl or a heteroaromatic ring (e. g. to form a quinolinyl or indolyl group).

Heteroaryl is an aromatic 5- or 6-membered ring, in which 1, 2 or 3 ring atoms are hetero atoms independently selected from O, N and S, such as pyrrolyl, thiazolyl, oxazolyl, pyrimidyl or preferably pyridyl. It can also be fused with a cycloalkyl or an aromatic or heteroaromatic ring (e. g. to form a quinolinyl or indolyl group).

Any non-cyclic carbon containing group or moiety with more than 1 carbon atom is straight-chain or branched.

Unless defined otherwise, carbon containing groups, moieties or molecules contain 1 to 8, preferably 1 to 6, more preferably 1 to 4, preferably 1 or 2, carbon atoms.

In preferred embodiments, which are preferred independently, collectively or in any combination or sub-combination, the invention relates to a compound of the formula I, in free form or in salt form, in which (1) $R_1$ is halogen, $C_1$-$C_8$alkyl, halo-$C_1$-$C_6$alkyl, $C_1$-$C_6$alkoxy-$C_1$-$C_6$alkyl, $C_3$-$C_6$cycloalkyl, $C_3$-$C_6$cycloalkyl-$C_1$-$C_6$alkyl, $C_1$-$C_6$alkylamino, pyrrolidinyl, tetrahydrofuryl or tetrahydrothienyl, preferably $C_1$-$C_8$alkyl, more preferably $C_1$-$C_4$alkyl, preferably isopropyl;

(2) $R_2$ is an aryl or heteroaryl group, which is optionally substituted by 1, 2 or 3 substituents, selected from the group consisting of halogen, $C_1$-$C_6$alkyl, halo-$C_1$-$C_6$alkyl, hydroxy, hydroxy-$C_1$-$C_6$alkyl, $C_1$-$C_6$alkoxy, $C_1$-$C_6$alkoxy-$C_1$-$C_6$alkyl, halo-$C_1$-$C_6$alkoxy, $C_1$-$C_6$alkylthio, halo-$C_1$-$C_6$alkylthio, $C_1$-$C_6$alkylsulfinyl, halo-$C_1$-$C_6$alkylsulfinyl, $C_1$-$C_6$alkylsulfonyl, halo-$C_1$-$C_6$alkylsulfonyl, $C_3$-$C_6$cycloalkyl, $C_3$-$C_6$cycloalkyl-$C_1$-$C_6$alkyl, $C_3$-$C_6$cycloalkoxy, $C_3$-$C_6$cycloalkoxy-$C_1$-$C_6$alkyl, amino, $C_1$-$C_6$alkylamino, di-($C_1$-$C_6$alkyl)amino, $C_1$-$C_6$alkoxycarbonylamino, cyano, formyl and $C_1$-$C_6$alkylcarbonyl, or which is substituted at two adjacent carbon atoms by —O—CH$_2$—O— or —O—CF$_2$—O—, preferably a phenyl, naphthyl, pyridyl, pyrimidyl, pyrrolyl, oxazolyl or thiazolyl group, which is optionally substituted by 1, 2 or 3 substituents, selected from the group consisting of halogen, $C_1$-$C_6$alkyl, halo-$C_1$-$C_6$alkyl, hydroxy, hydroxy-$C_1$-$C_6$alkyl, $C_1$-$C_6$alkoxy, $C_1$-$C_6$alkoxy-$C_1$-$C_6$alkyl, $C_1$-$C_6$alkylthio, amino, $C_1$-$C_6$alkoxycarbonylamino, cyano, formyl and $C_1$-$C_6$alkylcarbonyl, or which is substituted at two adjacent carbon atoms by —O—CH$_2$—O—, more preferably phenyl, which is substituted by 1, 2 or 3 substituents, selected from the group consisting of halogen and cyano, preferably phenyl, which is monosubstituted by halogen or cyano, more preferably phenyl, which is monosubstituted by chloro or cyano, preferably phenyl, which is monosubstituted in the 4-position by chloro or cyano;

(3) $R_3$ is hydrogen, hydroxy or $C_1$-$C_6$alkoxy, preferably hydrogen;

(4) $R_4$ is hydrogen, formyl, $C_1$-$C_6$alkylcarbonyl or benzyl, the phenyl group of which is optionally substituted by 1, 2 or 3 substituents, selected from the group consisting of halogen, $C_1$-$C_6$alkyl, halo-$C_1$-$C_6$alkyl, hydroxy, hydroxy-$C_1$-$C_6$alkyl, $C_1$-$C_6$alkoxy, $C_1$-$C_6$alkoxy-$C_1$-$C_6$alkyl, halo-$C_1$-$C_6$alkoxy, $C_1$-$C_6$alkylthio, halo-$C_1$-$C_6$alkylthio, $C_1$-$C_6$alkylsulfinyl, halo-$C_1$-$C_6$alkylsulfinyl, $C_1$-$C_6$alkylsulfonyl, halo-$C_1$-$C_6$alkylsulfonyl, $C_3$-$C_6$cycloalkyl, $C_3$-$C_6$cycloalkyl-$C_1$-$C_6$alkyl, $C_3$-$C_6$cycloalkoxy, $C_3$-$C_6$cycloalkoxy-$C_1$-$C_6$alkyl, amino, $C_1$-$C_6$alkylamino, di-($C_1$-$C_6$alkyl)amino, $C_1$-$C_6$alkoxycarbonylamino, cyano, formyl and $C_1$-$C_6$alkylcarbonyl, or is substituted at two adjacent carbon atoms by —O—CH$_2$—O— or —O—CF$_2$—O—, preferably hydrogen, formyl, $C_1$-$C_6$alkylcarbonyl or benzyl, more preferably hydrogen or formyl, preferably hydrogen;

(5) $R_5$ and $R_6$, taken together, represent, together with the three-membered moiety —N—C—C—, to which they are attached, a five-, six-, seven- or eight-membered, partially or fully unsaturated, optionally substituted, heterocyclic ring, which contains 1 ring nitrogen atom and optionally either 1 further ring nitrogen, oxygen or sulfur atom or 2 further ring nitrogen atoms, in which heterocyclic ring each ring oxygen or sulfur atom is bonded to 2 ring carbon atoms, the optional substituents of the said heterocyclic ring being selected from the group consisting of halogen, $C_1$-$C_6$alkyl, halo-$C_1$-$C_6$alkyl, hydroxy-$C_1$-$C_6$alkyl and oxo, preferably $R_5$ and $R_6$, taken together, represent, together with the three-membered moiety —N—C—C—, to which they are attached, a five-, six- or seven-membered, partially or fully unsaturated, optionally substituted, heterocyclic ring, which contains 1 ring nitrogen atom and optionally either 1 further ring nitrogen, oxygen or sulfur atom or 2 further ring nitrogen atoms, in which heterocyclic ring each ring oxygen or sulfur atom is bonded to 2 ring carbon atoms, the optional substituents of the said heterocyclic ring being selected from the group consisting of halogen, $C_1$-$C_6$alkyl, halo-$C_1$-$C_6$alkyl, hydroxy-$C_1$-$C_6$alkyl and oxo, more preferably N—$R_5$ and $R_6$—, taken together, represent a moiety N—X—O— (Ibb), in which —X— is —C(=O)— or —(CH$_2$)$_a$—, in which a is 2 or 3 and in which any methylene group, independently from any other methylene group in the moiety Ibb, is, optionally, mono-substituted by oxo or substituted by 1 or 2 substituents, selected from the group consisting of halogen, $C_1$-$C_6$alkyl, halo-$C_1$-$C_6$alkyl and hydroxy-$C_1$-$C_6$alkyl, or N—$R_5$ and $R_6$—, taken together, represent a moiety N—C($R_a$)=C($R_b$)— (Idd), in which $R_a$ is hydrogen, $C_1$-$C_6$alkyl, halo-$C_1$-$C_6$alkyl or hydroxy-$C_1$-$C_6$alkyl and $R_b$ is hydrogen, $C_1$-$C_6$alkyl, halo-$C_1$-$C_6$alkyl or hydroxy-$C_1$-$C_6$alkyl, or N—$R_5$ and $R_6$—, taken together, represent a moiety N—C($R_c$)=N— (Iee), in which $R_c$ is hydrogen, $C_1$-$C_6$alkyl or halo-$C_1$-$C_6$alkyl, or N—$R_5$ and $R_6$—, taken together, represent a moiety N—N=C($R_d$)— (Iff), in which $R_d$ is hydrogen, $C_1$-$C_6$alkyl or halo-$C_1$-$C_6$alkyl, or N—$R_5$ and $R_6$—, taken together, represent a moiety N—N=C($R_f$)— (Ig), in which $R_f$ is halogen, or N—$R_5$ and $R_6$—, taken together, represent a moiety N—N=N— (Ih) or N—$R_5$ and $R_6$—, taken together, represent a moiety N—(CH$_2$)$_2$—N(H)—C($R_g$)H— (Iii), in which $R_g$ is hydrogen, $C_1$-$C_6$alkyl or halo-$C_1$-$C_6$alkyl, preferably N—$R_5$ and $R_6$—, taken together, represent a moiety N—X—O— (Ibb), in which —X— is —C(=O)— or —(CH$_2$)$_a$—, in which a is 2 or 3 and in which any methylene group, independently from any other methylene group in the moiety Ibb, is, optionally, mono-substituted by oxo or substituted by 1 or 2 substituents, selected from the group consisting of $C_1$-$C_6$alkyl and hydroxy-$C_1$-$C_6$alkyl, or N—$R_5$ and $R_6$—, taken together, represent a moiety N—C($R_a$)=C($R_b$)— (Idd), in which $R_a$ is hydrogen and $R_b$ is $C_1$-$C_6$alkyl, or N—$R_5$ and $R_6$—, taken together, represent a moiety N—C($R_c$)=N— (Iee), in which $R_c$ is hydrogen, $C_1$-$C_6$alkyl or halo-$C_1$-$C_6$alkyl, or N—$R_5$ and $R_6$—, taken together, represent a moiety N—N=C($R_d$)— (Iff), in which $R_d$ is hydrogen or $C_1$-$C_6$alkyl, or N—$R_5$ and $R_6$—, taken together, represent a moiety N—N=C($R_f$)— (Ig), in which $R_f$ is halogen, or N—$R_5$ and $R_6$—, taken together, represent a moiety N—N=N— (Ih) or N—$R_5$ and $R_6$—, taken together, represent a moiety N—(CH$_2$)$_2$—N(H)—C($R_g$)H— (Iii), in which $R_g$ is hydrogen.

In especially preferred embodiments, the invention relates to one or more than one of the compounds of the formula I mentioned in the Examples hereinafter, in free form or in salt form.

The present invention relates also to a process for the preparation of a compound of the formula I, in free form or in salt form, which is characterized in that a) for the preparation of a compound of the formula I, in which N—$R_5$ and $R_6$—, taken together, represent a moiety N—(CH$_2$)$_a$—O— (Iaa), in which a is 2 or 3 and in which any methylene group, independently from any other methylene group in the moiety Iaa, is optionally substituted by 1 or 2 substituents, selected from the group consisting of halogen, $C_1$-$C_6$alkyl, halo-$C_1$-$C_6$alkyl and hydroxy-$C_1$-$C_6$alkyl, a compound of the formula

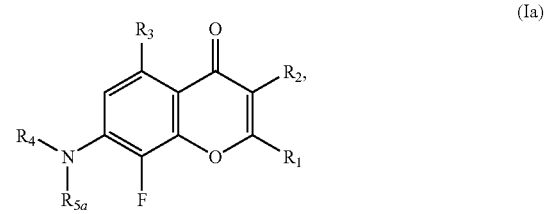

(Ia)

in which $R_1$, $R_2$, $R_3$ and $R_4$ have one of the meanings given for the formula I and N—$R_5$, represents a moiety N—(CH$_2$)$_a$—OH (Iaaa), in which a is 2 or 3 and in which any methylene group, independently from any other methylene group in the moiety Iaaa, is optionally substituted by 1 or 2 substituents, selected from the group consisting of halogen, $C_1$-$C_6$alkyl, halo-$C_1$-$C_6$alkyl and hydroxy-$C_1$-$C_6$alkyl, is intramolecularly cyclised or b) for the preparation of a compound of the formula I, in which N—$R_5$ and $R_6$—, taken together, represent a moiety N—X—O— (Ibb), in which —X— is —C(=O)— or —(CH$_2$)$_a$—, in which a is 2 or 3 and in which any methylene group, independently from any other methylene group in the moiety Ibb, is, optionally, mono-substituted by oxo or substituted by 1 or 2 substituents, selected from the group consisting of halogen, $C_1$-$C_6$alkyl, halo-$C_1$-$C_6$alkyl and hydroxy-$C_1$-$C_6$alkyl, a compound of the formula

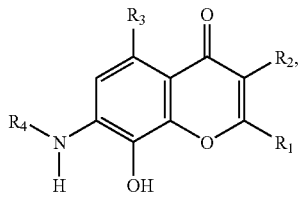

(Ib)

in which $R_1$, $R_2$, $R_3$ and $R_4$ have one of the meanings given for the formula I, is reacted with a compound of the formula $X_1$—X—$X_2$ (Ibbb), in which $X_1$ is halogen, $X_2$ is halogen and —X— has one of the meanings given for the moiety Ibb, or c) for the preparation of a compound of the formula I, in which $R_4$ is hydrogen, a compound of the formula I, in which $R_4$ is different from hydrogen, is converted into a compound of the formula I, in which $R_4$ is hydrogen, or d) for the preparation of a compound of the formula I, in which $R_4$ is hydrogen, in a compound of the formula

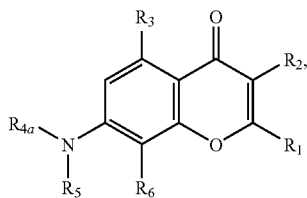

(Id)

in which $R_1$, $R_2$, $R_3$, $R_5$ and $R_6$ have one of the meanings given for the formula I and $R_{4a}$ is a protecting group, the protecting group $R_{4a}$ is removed or e) for the preparation of a compound of the formula I, in which N—$R_5$ and $R_6$—, taken together, represent a moiety N—C($R_c$)=N— (Iee), in which $R_c$ is hydrogen, $C_1$-$C_6$alkyl or halo-$C_1$-$C_6$alkyl, a compound of the formula

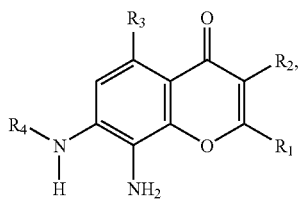

(Ie)

in which $R_1$, $R_2$, $R_3$ and $R_4$ have one of the meanings given for the formula I, is reacted with a compound of the formula HO—C($R_c$)=O (Ieee), in which $R_c$ has one of the meanings given for the moiety Iee, or f) for the preparation of a compound of the formula I, in which $R_4$ is hydrogen and N—$R_5$ and $R_6$—, taken together, represent a moiety N—N=C($R_d$)— (Iff), in which $R_d$ is hydrogen, $C_1$-$C_6$alkyl or halo-$C_1$-$C_6$alkyl, a compound of the formula

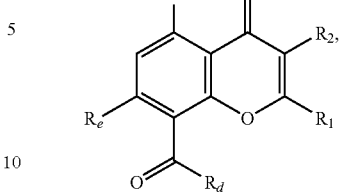

(If)

in which $R_1$, $R_2$ and $R_3$ have one of the meanings given for the formula I, $R_d$ has one of the meanings given for the moiety Iff and $R_e$ is 2,4,6-trimethylphenylsulfonyloxy or phenylsulfonyloxy, is reacted with hydrazine hydrate or g) for the preparation of a compound of the formula I, in which N—$R_5$ and $R_6$—, taken together, represent a moiety N—N=C($R_f$)— (Ig), in which $R_f$ is halogen, a compound of the formula I, in which N—$R_5$ and $R_6$—, taken together, represent a moiety N—N=C($R_d$)— (Iff), in which $R_d$ is hydrogen, is halogenated or h) for the preparation of a compound of the formula I, in which N—$R_5$ and $R_6$—, taken together, represent a moiety N—N=N— (Ih), a compound of the formula

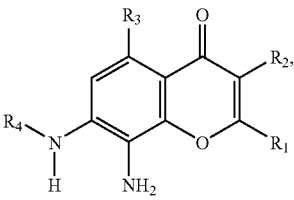

(Ie)

in which $R_1$, $R_2$, $R_3$ and $R_4$ have one of the meanings given for the formula I, is reacted with sodium nitrite or i) for the preparation of a compound of the formula I, in which N—$R_5$ and $R_6$—, taken together, represent a moiety N—(CH$_2$)$_2$—N(H)—C($R_g$)H— (Iii), in which $R_g$ is hydrogen, $C_1$-$C_6$alkyl or halo-$C_1$-$C_6$alkyl, in a compound of the formula

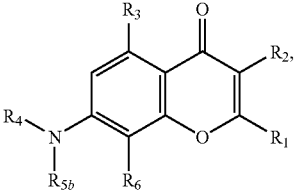

(Ii)

in which $R_1$, $R_2$, $R_3$ and $R_4$ have one of the meanings given for the formula I and N—$R_{5b}$ and $R_6$—, taken together, represent a moiety N—(CH$_2$)$_2$—N=C($R_g$)— (Iiii), in which $R_g$ has one of the meanings given for the moiety Iii, the —N=C ($R_g$)— double bond is hydrogenated or j) for the preparation of a compound of the formula I, in which $R_2$ is 4-cyanophenyl, a compound of the formula I, in which $R_2$ is 4-chlorophenyl, is converted into a compound of the formula I, in which $R_2$ is 4-cyanophenyl, and, in each of the variants a) through j), the final compound of the formula I is isolated in free form or in salt form.

All process steps described herein can be carried out under known reaction conditions, preferably under those specifically mentioned, in the absence of or usually in the presence of solvents or diluents, preferably such as are inert to the reagents used and able to dissolve these, in the absence or presence of catalysts, condensing agents or neutralizing agents, e. g., ion exchangers, typically cation exchangers, e. g., in the $H^+$ form, depending on the type of reaction and/or reactants at reduced, normal or elevated temperature, e. g., in the range from $-100°$ C. to about $250°$ C., preferably from about $-80°$ C. to about $150°$ C., e. g., at $-80°$ C. to $60°$ C., at room temperature, at $-20°$ C. to $40°$ C. or at the boiling point of the solvent used, under atmospheric pressure or in a closed vessel, where appropriate under pressure, and/or in an inert atmosphere, e. g., under argon or nitrogen, optionally under microwave irradiation.

The reactions can be effected according to conventional methods, for example as described hereinafter.

Variant a): The intramolecular cyclisation is carried out, for example, in the presence of a base, such as sodium hydride, in an appropriate solvent, such as N,N-dimethylformamide, N,N-dimethylacetamide or N-methylpyrrolidinone, and at a temperature in the range of from $0°$ C. to $200°$ C., optionally under microwave irradiation.

Variant b): The reaction is carried out, for example, in the presence of a base, such as triethylamine, potassium carbonate or cesium carbonate, in an appropriate solvent, such as dichloromethane, N,N-dimethylformamide, N,N-dimethylacetamide or N-methylpyrrolidinone, and at a temperature in the range of from $-20°$ C. to $180°$ C.

Variant c): The conversion is carried out, for example, in the presence of an acid, such as hydrochloric acid, in an appropriate solvent, for example in an alcohol, such as methanol, and at a temperature in the range of from $0°$ C. to $200°$ C.

Variant d): The removal of the group $R_{4a}$ is carried out, for example, by hydrogenation in the presence of an appropriate catalyst, such as palladium on activated carbon, in an appropriate solvent, such as tetrahydrofuran or ethanol, and at a temperature in the range of from $-20°$ C. to $180°$ C.

Variant e): The reaction is carried out, for example, at a temperature in the range of from $0°$ C. to $200°$ C., optionally in the presence of an acid, such as hydrochloric acid.

Variant f): The reaction is carried out, for example, in the presence of ammonium acetate and a dehydrating agent, such as magnesium sulfate or molecular sieves, in an appropriate solvent, such as ethanol, toluene or xylenes, and at a temperature in the range of from $0°$ C. to $250°$ C., optionally under microwave irradiation.

Variant g): The halogenation is carried out, for example, in the presence of a suitable halogen donor, such as iodine, in the presence of a base, such as potassium hydroxide, in an appropriate solvent, such as N,N-dimethylformamide, N,N-dimethylacetamide or N-methylpyrrolidinone, and at a temperature in the range of from $-20°$ C. to $180°$ C.

Variant h): The reaction is carried out, for example, in the presence of an acid, such as acetic acid, and at a temperature in the range of from $-20°$ C. to $50°$ C.

Variant i): The hydrogenation is carried out, for example, in the presence of a suitable hydrogen donor, such as sodium borohydride, sodium triacetoxyborohydride, sodium cyanoborohydride or hydrogen, in an appropriate solvent, such as methanol, and at a temperature in the range of from $-20°$ C. to $120°$ C.

Variant j): The conversion is carried out, for example, in the presence of a metal cyanide, such as zinc cyanide, in the presence of a palladium catalyst, such as tetrakis(triphenylphosphine)palladium (0) or tris(dibenzylideneacetone)dipalladium (0), optionally in the presence of a ferrocene, such as 1,1'-bis(diphenylphosphino)ferrocene, in an appropriate solvent, such as N,N-dimethylformamide, N,N-dimethylacetamide or N-methylpyrrolidinone, and at a temperature in the range of from $0°$ C. to $250°$ C., optionally under microwave irradiation.

Detailed reaction conditions are described in the Examples.

The working-up of the reaction mixtures and the purification of the compounds thus obtainable may be carried out in accordance with known procedures.

Salts may be produced from the free compounds in known manner, and vice-versa.

Compounds of the formula I can also be prepared by further conventional processes, which processes are further aspects of the invention, e. g. as described in the Examples.

Compounds of the formula I in free form and their pharmaceutically acceptable salts, hereinafter referred to as agents of the invention, exhibit valuable pharmacological properties when tested in vitro and in animals, and are therefore useful as pharmaceuticals.

In particular, the agents of the invention are antagonists of human, rat or guinea pig transient receptor potential vanilloid receptor 1 (also known as TRPV1 receptor, vanilloid receptor 1, VR1 or capsaicin receptor), as demonstrated by their ability to inhibit capsaicin and low pH activation of the TRPV1 ion channel, e. g., as follows:

Chinese Hamster Ovary-K1 (CHO-K1) cells, transfected to express either the human, rat or guinea pig TRPV1 receptor, were grown in Minimal Essential Media (MEM) alpha medium without nucleosides supplemented with fetal calf serum (10%), 2 mM L-glutamine, 100 IU/mL penicillin, 100 μg/ml streptomycin and 350-700 μg/ml geneticin. All reagents were supplied by Invitrogen. Cells were grown in T-175 flasks or Costar black, clear-bottomed 96-well view plates and maintained at $37°$ C. in a 90% humidified incubator with an atmosphere of 5% $CO_2$ and 95% air. The cells were passaged twice a week at a ratio of 1:10 to 1:20 to maintain steady growth. For experimentation, cells were harvested at approximately 80% confluency and plated onto view plates at 40,000 cells per well in 100 μL media and grown overnight.

Calcium Mobilisation Assay

On the day of the capsaicin assay, media was aspirated and cells were washed with 100 μl 10 mM N-2-(hydroxyethylpiperazine-N'-[2-ethane-sulfonic acid] (HEPES) buffered Hank's Balanced Salt Solution (HBSS), pH 7.4. Cells were then incubated for 40 minutes with 2.3 μM of the ratiometric calcium binding dye fura-2/AM (from Molecular Probes), made up in HEPES buffered HBSS, containing 0.01% pluronic F-127. For the pH assay, HEPES was omitted and the pH of HBSS adjusted to 7.4. After washing twice with 100 μl assay buffer, cells were incubated for 10 minutes with 100 μl of test compounds (made up in HBSS, pH 7.4), in duplicate, at concentrations between 0.001 and 30 μM. The plate was then placed in a Molecular Devices Flexstation. The TRPV1 receptor was stimulated by application of either capsaicin or low pH. For testing the effect of compounds for possible antagonism, capsaicin was used at the $EC_{80}$ concentration which was 0.05 μM for the rat TRPV1 receptor, and 0.1 μM for the human and guinea pig. For pH experiments, a low pH buffered solution [60 mM 2-[N-morpholino]ethane sulfonic acid (MES) in HBSS] was added to the assay wells to give a final pH of 5.5.

For determinations of antagonist $IC_{50}$ values (concentrations of antagonist that inhibit responses to either pH 5.5 or capsacin by 50%), at least 10 antagonist concentrations were measured in duplicate. The response in the presence of the antagonist was calculated as a percentage of the control response to capsaicin or low pH and was plotted against the concentration of antagonist. The $IC_{50}$ was estimated by non-linear regression analysis to sigmoidal-logistic curves by Activity-Base software (v5.0.10) or Microcal Origin (v7.03). These values were averaged (means and standard error of the mean) for at least three independent experiments.

The agents of the invention, e. g., the compounds of Examples 1 to 15, are TRPV1 receptor antagonists having $IC_{50}$ values in the range of from 0.004 to 30 μM. For example, the compound of the formula I obtainable according to Example 8 has $IC_{50}$ values of 0.054 μM (pH 5.5) and 0.068 μM (capsacin), respectively.

In view of the above, the agents of the invention are useful as vanilloid receptor blockers, e. g., in the prevention and treatment of diseases and conditions in which vanilloid receptor activation plays a role or is implicated. Such conditions include, in particular, pain, e. g., bone and joint pain (osteoarthritis), cancer pain, myofascial pain (muscular injury, fibromyalgia) and perioperative pain (general surgery, gynecologic surgery).

The agents of the invention are particularly useful in the treatment or prevention of chronic pain, especially inflammatory, e. g., chronic inflammatory pain; inflammatory diseases, e. g., inflammatory airways disease, e. g., chronic obstructive pulmonary disease (COPD), or in asthma; cough; urinary incontinence; migraine; visceral disorders, e. g., inflammatory bowel disease; rhinitis; cystitis, e. g. interstitial cystitis; pancreatitis; uveitis; inflammatory skin disorders; and rheumatoid arthritis.

The agents of the invention are thus useful as vanilloid receptor antagonists, e. g., for the treatment of pain of various genesis or aetiology and as anti-inflammatory and/or anti-edemic agents for the treatment of inflammatory reactions, diseases or conditions, as well as for the treatment of allergic responses. Having regard to their analgesic/anti-inflammatory profile, they are useful for the treatment of inflammatory pain, for the treatment of hyperalgesia and, in particular, for the treatment of severe chronic pain. They are, e. g., useful for the treatment of pain, inflammation and/or oedema consequential to trauma, e. g., associated with burns, sprains, fractures or the like, subsequent to surgical intervention, e. g., as post-operative analgesics, as well as for the treatment of inflammatory pain of diverse genesis, e. g., for the treatment of osteo and rheumatoid arthritis and rheumatic disease, tenosynovitis and gout. They are further suitable as analgesics for the treatment of pain associated with, e. g., angina, menstruation or cancer. As anti-inflammatory/anti-oedema agents, they are further useful, e. g., for the treatment of inflammatory skin disorders, e. g., psoriasis and eczema.

As vanilloid receptor blockers, the agents of the invention are also useful as smooth muscle relaxants, e. g., for the treatment of spasm of the gastrointestinal tract or uterus, e. g., in the therapy of Crohn's disease, ulcerative colitis or pancreatitis.

The agents of the invention are in particular useful as agents for the therapy of airways hyperreactivity and for the treatment of inflammatory events associated with airways disease, in particular, asthma. In addition, the agents of invention may, e. g., be used for the control, restriction or reversal of airways hyperreactivity in asthma.

Inflammatory or obstructive airways diseases to which the present invention is applicable include asthma of whatever type or genesis including both intrinsic and, especially, extrinsic asthma. Thus, the agents of the invention are useful for the treatment of allergic asthma, as well as, e. g., exercise induced asthma, occupational asthma, asthma induced following bacterial infection, other non-allergic asthmas and "wheezy-infant syndrome".

Efficacy in the treatment of asthma will be evidenced by reduced frequency or severity of symptomatic attack, e. g., of acute asthmatic or bronchoconstrictor attack and by reduced requirement for other, symptomatic therapy, e. g., anti-inflammatory, e. g., corticosteroid; or bronchodilator, e. g., β2 adrenergic, therapy.

Inflammatory or obstructive airways diseases to which the present invention is applicable further include pneumoconiosis (an inflammatory, commonly occupational, disease of the lungs, frequently accompanied by repeated inhalation of dusts) of whatever type or genesis including, e. g., aluminosis, anthracosis, asbestosis, chalicosis, ptilosis, siderosis, silicosis, tabacosis and, in particular, byssinosis.

Further inflammatory or obstructive airways diseases and conditions for which the agents of the invention may be used include adult respiratory distress syndrome (ARDS), chronic obstructive pulmonary or airways disease (COPD or COAD), and bronchitis. The agents of the invention may also be used for the treatment of allergic and vasomotor rhinitis.

In addition to the foregoing, the agents of the invention are also indicated for use in the therapy of septic shock, e. g., as anti-hypovolaemic and/or anti-hypotensive agents; in the treatment of inflammatory bowel disease; cerebral oedema; headache; migraine; inflammatory skin disease, such as eczema and psoriasis; inflammatory disorders of the gut, e. g., irritable bowel syndrome; Crohn's disease; ulcerative colitis; and cystitis, e. g., interstitial cystitis, nephritis and uveitis.

Such conditions include, in particular, acute or chronic pain of somatic or visceral origin, inflammatory or obstructive airways disease, urinary incontinence or over-active bladder, inflammatory skin diseases, inflammatory disorders of the gastrointestinal tract, diabetes, obesity and obesity-related diseases, psychiatric disorders, and treatment of the consequences exposure to VR1 agonists.

The agents of the invention are useful in the prevention and treatment of diseases and conditions in which human VR1 activation plays a role or is implicated, and therefore susceptible to treatment by the modulation (preferably antagonism) of VR1 receptors. Such conditions include, in particular, acute or chronic pain of somatic or visceral origin, inflammatory or obstructive airways disease, urinary incontinence or over-active bladder, inflammatory skin diseases, inflammatory disorders of the gastrointestinal tract, diabetes, obesity and obesity-related diseases, psychiatric disorders, and treatment of the consequences exposure to VR1 agonists. Such conditions include chronic pain with an inflammatory component such as rheumatoid arthritis; bone and joint pain (osteoarthritis); post-surgical pain; musculo-skeletal pain such as fibromyalgia; myofascial pain syndromes; headache, including migraine, acute or chronic tension headache, cluster headache, temporomandibular pain, and maxillary sinus pain; ear pain; episiotomy pain; burns, and especially primary hyperalgesia associated therewith; deep and visceral pain, such as heart pain, muscle pain, eye pain, orofacial pain, abdominal pain, gynaecological pain, such as dysmenorrhoea, and labour pain; pain associated with the urogenital tract such as cystitis and vulvadynia; inflammatory skin disorders, for example psoriasis and eczema, or itch of non-specific origin; chronic pain associated with nerve injury and/or diseases affecting the nervous system, such as neuropathic pain associated with post-herpetic neuralgia, diabetic neuropathy, chemotherapy-induced neuropathy, amputations ("phantom limb pain"), nerve entrapment and brachial plexus avulsions, low back pain, sciatica and ankylosing spondylitis, reflex sympathetic dystrophy and other chronic nerve injuries; complex regional pain syndromes; central nervous system pain, such as pain due to spinal cord or brain stem damage, or stroke; gout; scar pain; pain associated with carcinoma, often referred to as cancer pain; respiratory diseases including asthma, aluminosis, anthracosis, inflammatory airways disease, e. g. Chronic Obstructive Pulmonary Disease; chronic bronchitis, asbestosis, chalicosis, ptilosis, siderosis, silicosis, tabacosis, byssinosis; rhinitis including allergic rhinitis such as seasonal and perennial rhinitis, and non-allergic rhinitis; cough, either idiopathic or associated with respiratory diseases such as COPD, asthma, cystic fibrosis, cancer, or gastrointestinal disturbances such as gastro-oesophageal reflux; autoimmune diseases; gastrointestinal disorders including, but not restricted to irritable bowel syndrome, Crohn's disease, ulcerative colitis, pancreatitis, inflammatory bowel disease; diseases of the urogenital tract, particularly cystitis; urinary incontinence, bladder hypersensitivity and overactive bladder.

The agents of the invention are particularly useful in the treatment or prevention of chronic pain with an inflammatory component such as rheumatoid arthritis; bone and joint pain (osteoarthritis); post-surgical or trauma pain including dental pain e. g. following third molar extraction, post mastectomy pain and pain associated with sprains or fractures; musculoskeletal pain such as fibromyalgia; myofascial pain syndromes; headache, including migraine, acute or chronic tension headache, cluster headache, temporomandibular pain, and maxillary sinus pain; ear pain; episiotomy pain; burns, and especially primary hyperalgesia associated therewith; deep and visceral pain, such as heart pain, muscle pain, eye pain, orofacial pain, abdominal pain, gynaecological pain, such as dysmenorrhoea, and labour pain; hemorrhoids; pain associated with the urogenital tract such as cystitis and vulvadynia; chronic pain associated with nerve injury and/or diseases affecting the nervous system, such as neuropathic pain associated with post-herpetic neuralgia, diabetic neuropathy, chemotherapy-induced neuropathy, amputations ("phantom limb pain"), nerve entrapment and brachial plexus avulsions, low back pain, sciatica and ankylosing spondylitis, reflex sympathetic dystrophy and other chronic nerve injuries; complex regional pain syndromes; Glossodynia or burning mouth syndrome; central nervous system pain, such as pain due to spinal cord or brain stem damage, multiple sclerosis or stroke; gout; scar pain; pain associated with carcinoma, often referred to as cancer pain; pain associated with viral (e.g. HIV)-induced neuropathy, alcohol and narcotic abuse; pain and other symptoms associated with sun or UV burn, exposure to VR1 agonist (e.g. capsaicin, acid, tear gas, noxious heat or pepper spray), snake, spider or insect bite and jellyfish sting.

Urinary incontinence ("UI") to be treated in accordance with the invention is a broad term that covers a range of disorders and symptoms including urge UI, stress UI, mixed urge/stress UI, neurogenic UI, bladder detrusor hyperreflexia (neurogenic detrusor overactivity), detrusor instability (idiopathic detrusor overactivity), decreased bladder compliance, weakness of urethal sphincter, urinary outlet obstruction, interstitial cystitis, sensory urgency, motor uregency, nocturia, and bladder-related visceral pain.

Urinary incontinence ("UI") or overactive bladder to be treated in accordance with the invention is a broad term that covers a range of disorders and symptoms including urge UI, stress UI, mixed urge/stress UI, neurogenic UI, bladder detrusor hyperreflexia (neurogenic detrusor overactivity), detrusor instability (idiopathic detrusor overactivity), decreased bladder compliance, weakness of urethal sphincter, urinary outlet obstruction, interstitial cystitis, nephritis, uveitis, sensory urgency, motor urgency, nocturia, and bladder-related visceral pain.

Gastrointestinal disorders to be treated in accordance with the invention include those associated with gastrointestinal hypersensitivity and/or altered motor responses (including electrolyte/water secretion), for example functional bowel disorders and functional gastrointestinal disorders, such as irritable bowel syndrome (IBS), constipation, diarrhoea, functional dyspepsia, gastro-oesophageal reflux disease, functional abdominal bloating, and functional abdominal pain, other conditions associated with visceral hypersensitivity such as post-operative visceral pain, visceral smooth muscle spasms, ulcerative colitis, Crohn's disease, ulcers, Hirschsprung's disease and functional bowel disorders (not necessarily associated with visceral hypersensitivity or abnormal motor responses).

Gastrointestinal disorders to be treated in accordance with the invention include those associated with gastrointestinal hypersensitivity, visceral pain and/or altered motor responses (including electrolyte/water secretion) such as functional bowel disorders and functional gastrointestinal disorders, including irritable bowel syndrome (IBS), functional dyspepsia, heartburn, non-erosive reflux disease, intestinal pseudoobstruction, functional abdominal bloating, and functional abdominal pain; other conditions associated with visceral hypersensitivity including gastro-oesophageal reflux disease and emesis, oesophagitis, post-operative visceral pain, post-operative ileus, visceral smooth muscle spasms, ulcerative colitis, Crohn's disease, ulcers, chronic constipation, diarrhea, early satiety, epigastric pain, nausea, vomiting, burbulence, anal incontinence, faecal urgency and rectal hypersensitivity, gastroparesis, e. g. diabetic gastroparesis, pancreatitis and Hirschsprung's disease.

The agents of the invention are useful in the prevention and treatment of an altered gastrointestinal sensitivity, motility and secretion and abdominal disorders including, but not limited to, heartburn, bloating, postoperative ileus, abdominal pain and discomfort, early satiety, epigastric pain, nausea, vomiting, burbulence, regurgitation, intestinal pseudoobstruction, anal incontinence, GERD, IBS, dyspepsia, chronic constipation or diarrhea, gastroparesis, e. g. diabetic gastroparesis, ulcerative colitis, Crohn's disease, ulcers, Hirschsprung's disease and the visceral pain associated therewith.

The agents of the invention are also useful as agents for the therapy of hyperreactive, inflammatory or obstructive airways diseases including asthma, inflammatory airways disease, e.g. chronic obstructive pulmonary or airways disease (COPD or COAD), adult respiratory distress syndrome (ARDS), chronic bronchitis, pneumoconiosis, e. g. aluminosis, anthracosis, asbestosis, chalicosis, ptilosis, siderosis, silicosis, tabacosis, byssinosis; rhinitis including allergic rhinitis such as seasonal and perennial rhinitis, and non-allergic rhinitis; cough, either idiopathic or associated with respiratory diseases such as COPD, asthma, cystic fibrosis, cancer, or gastrointestinal disturbances such as gastro-oesophageal reflux.

The agents of the invention may also have therapeutic benefit in inflammatory skin disorders, for example psoriasis and eczema, or itch of non-specific origin; contact dermatitis and hypersensitivity; autoimmune or inflammatory diseases, including Crohn's disease, ulcerative colitis and Gullian Barre Syndrome; multiple chemical sensitivity, neurological diseases like anxiety, panic disorders, depression, schizophrenia, cognition, Parkinson's Disease and Alzheimer's Disease; hair loss; diabetes; obesity and obesity-related diseases; as anti-spasmodics, e.g. for the treatment of spasm of the gastrointestinal tract or uterus; for the therapy of septic shock, e.g. as anti-hypovolaemic and/or anti hypotensive agents; cerebral oedema.

For the above-mentioned indications, the appropriate dosage will of course vary depending upon, e. g., the compound employed, the host, the mode of administration and the nature and severity of the condition being treated. However, in general, satisfactory results in animals are indicated to be obtained at a daily dosage of from about 0.05 mg/kg to about 150 mg/kg, preferably from about 0.1 mg/kg to about 100 mg/kg, animal body weight. In larger mammals, e. g., humans, an indicated daily dosage is in the range from about 0.5 mg to about 5,000 mg, preferably from about 1 mg to about 500 mg of an agent of the invention, conveniently administered, e. g., in divided doses up to four times a day or in sustained-release form.

The agents of the invention can be administered in vivo either alone or in combination with other pharmaceutical agents, e.g. agents effective in the treatment of diseases and conditions in which the human VR1 activation plays a role or is implicated, such as cyclooxygenase inhibitors, including specific COX-2 inhibitors (e. g. celecoxib, rofecoxib, lumiracoxib, and valdecoxib) or in general nonsteroidal anti-inflammatory drugs (NSAIDs) (e. g. acetylsalicylic acid, propionic acid derivatives), anti-migraine agents such as 5-HTi agonists and CGRP antagonists, tricyclic antidepressants (e. g. clomipramine, amoxapine, nortripyline, amitriptyline, imipramine, desipramine, doxepin, trimipramine, protripyline, Anafranil®, Asendin®, Aventyl®, Elavil®, Endep®, Norfranil®, Norpramin®, Pamelor®, Sinequan®, Surmontil®, Tipramine®, Tofranil®, Vivactil®, Tofranil-PM®), selective serotonic reuptake inhibitors (e.g. fluoxetine), selective noradrenaline reuptake inhibitors (e.g. duloxetine), anticonvulsants (e.g. gabapentin, pregabalin, oxcarbazepine, carbamazepine), $GABA_B$ agonists (e.g. L-baclofen), opioids (e.g. morphine), $CB_1$ receptor agonists, bradykinin receptor B1 or B2 antagonists, substance P antagonists.

The agents of the invention can be administered in vivo either alone or in combination with other pharmaceutical agents, e.g. agents effective in the treatment of diseases and conditions in which the human VR1 activation plays a role or is implicated. A suitable combination consists of a compound of the present invention with a compound selected from the class or individuals from the following list:

Dopamine $D_2$ antagonists, eg domperidone, metoclopramide and itopride;

$5HT_4$ receptor agonists, eg cisapride, cinitapride, mosapride, renzapride, prucalopride, tegaserod, and compounds described in WO 2005068461 (Aryx), e. g. AT-7505, US 2005228014 and WO 2005080389 (Theravance), e. g. TDI-2749, US 2006100426, US 2006100236, US 2006135764, US 20060183901, WO 200610827, WO 2006094063, WO 2006090224, WO2006090279, US 2005277671, WO 2005092882, WO 2005073222, JP 2005104896, JP 2005082508, WO 2005021539, JP 2004277319, JP 2004277318, WO 2004026869 and EP 1362857;

$5HT_3$ agonists, eg pumosetrag;

$CCK_A$ receptor antagonists, eg loxiglumide and dexioxiglumide;

Motilin receptor agonists, eg motilin, atilmotilin, erythromycin, alemcinal, mitemcinal, KOS-2187 and compounds described in WO 2005060693;

μ-opioid antagonists, eg alvimopan and methylnaltrexone;

Opioid agonists, eg asimadoline, loperamide and codeine;

CRF-1 receptor antagonists, eg GSK876008 and compounds described in WO 2004069257, WO 9940089, U.S. Pat. No. 6,844,351, WO 2005013997, WO 2005014557, WO 2005023806, WO 2005026126, WO 2005028480, WO 2005044793, WO 2005051954, WO 2005051954, WO 2005115399, WO 2005028480, WO 2005023806, WO 2006044958, US 20060211710 and WO 2006108698;

Glutamate receptor antagonists, eg AZD9272 and compounds described in WO 9902497, WO 2000020001, WO 200304758 and WO 2005030723;

Neurokinin receptor antagonists, eg casopitant, nepadutrent saredutant, DNK-333, SLV-317, SLV321, SLV317 and compounds described in EP 96-810237;

$5HT_3$ receptor antagonists, eg alosetron, cilansetron, ramosetron, azasetron, ondansetron, granisetron tropisetron and DDP225;

Histamine $H_2$ antagonists, eg famotidine, cimetidine, ranitidine and nizatidine;

Histamine $H_4$ antagonists, eg JNJ7777120, JNJ10191584 and compounds described in US 2006111416, WO 2006050965, WO 2005092066, WO 2005054239 US 2005070550, US 2005070527 and EP 1505064;

Proton pump inhibitors, eg omeprazole, lansoprazole, rabeprazole, tentoprazole, pantoprazole, esomeprazole, revaprazan soraprazan and AGN201904;

Chloride channel activators, eg lubiprostone;

Guanylate cyclase activators, eg linaclotide;

Muscarinic antagonists, eg darifenacin, solifenacin, atropine, dicycloverine, hycosine butyl bromide, propantheline, oxybutinin, cimetropium bromide, pinaverium bromide and otilonium bromide;

Antispasmodics, eg mebeverine, tiropramide, alverine and peppermint oil; Stimulant laxatives, eg bisacodyl;

Osmotic laxatives, eg activated charcoal with sorbitol, lactulose, magnesium hydroxide and phosphate buffered saline;

Faecal softeners, eg senna concentrate, liquid paraffin and arachis oil;

Absorbents and fibre supplements, eg bulk fibre laxatives such as bran, methylcellulose, ispaghula husk and sterculia;

Antacids, eg aluminium, magnesium and calcium antacids, simeticone and alginate containing preparations;

GI relaxants, eg cholestyramine resin;

Bismuth compounds, eg bismuth subsalicylate;

Vanilloid receptor antagonists, eg compounds described in WO 2002076946, WO 2004033435, WO 2005121116 and WO 2005120510;

Anticonvulsants, eg carbamazepine, oxcarbemazepine, lamotrigine, gabapentin, and pregabalin;

NSAIDS, eg aspirin, acetometaphen, ibuprofen, diclofenac, naproxen, flurbiprofen, indomethacin, piricoxam, ketoprofen, sulindac and diflunisal;

COX-2 inhibitors eg celecoxib, rofecoxib, lumiracoxib, valdecoxib, etoricoxib and compounds described in WO 2004048314;

Opiates, eg morphine, buprenorphine, diamorphine, dihydrocodeine, fentanyl and pethidine;

$GABA_b$ modulators, eg racemic and (R)-baclofen, AZD3355, XP19986 and compounds described in WO 2006001750 and WO 2004000856;

CB receptor ligands, eg compounds described in WO 2002042248 and WO 2003066603;

Calcium channel blockers, eg ziconotide, AGI0-003, PD-217014 and compounds described in WO 2006038594, WO 2006030211 and WO 2005068448;

Sodium channel blockers, eg lamotrigine and compounds described in WO 2006023757, WO 2005097136, JP 2005206590 and WO 2005047270;

Tricyclic antidepressants, e.g. clomipramine, amoxapine, nortripyline, amitriptyline, imipramine, desipramine, doxepin, trimipramine and protripyline;

Selective serotonin reuptake inhibitors, eg fluoxetine, paroxetine, citaprolam, sertaline, fluvoxamine, duloxetine;

Anxiolytic agents, eg milnacipran, tianeptine, MC1-225 and dextofisopam;

CGRP antagonists, eg olcegepant and cizolirtine;

$5HT_{1d}$ antagonists, eg almotriptan, eletriptan, frovatriptan, naratriptan, rizatriptan, sumatriptan and zolmatriptan; and Bradykinin receptor antagonists, eg compounds described in WO 2000075107, WO 2002092556 and WO 20050851298.

The pharmaceutical compositions for separate administration of the combination partners and for the administration in a fixed combination, i. e., a single galenical composition comprising at least two combination partners, according to the invention can be prepared in a manner known per se and are those suitable for enteral, such as oral or rectal, and parenteral administration to mammals, including man, comprising a therapeutically effective amount of at least one pharmacologically active combination partner alone or in combination with one or more pharmaceutically acceptable carriers, especially suitable for enteral or parenteral application.

Pharmaceutical compositions contain, e. g., from about 0.1% to about 99.9%, preferably from about 20% to about 60%, of the active ingredients. Pharmaceutical preparations for the combination therapy for enteral or parenteral administration are, e. g., those in unit dosage forms, such as tablets including sugar-coated tablets, capsules, suppositories and ampoules. These are prepared in a manner known, per se, e. g., by means of conventional mixing, granulating, sugar-coating, dissolving or lyophilizing processes. It will be appreciated that the unit content of a combination partner contained in an individual dose of each dosage form need not in itself constitute an effective amount since the necessary effective amount can be reached by administration of a plurality of dosage units.

A further aspect of the instant invention involves the novel compositions comprising a pharmaceutically acceptable carrier or diluent and a therapeutically effective amount of an agent of the invention.

In accordance with the foregoing, the present invention also provides:

(1) An agent of the invention for use as a vanilloid receptor blocker, e. g., for use in any of the particular indications set forth hereinabove;

(2) An agent of the invention for the treatment of a disease or condition in which vanilloid receptor plays a role or is implicated;

(3) A method for the treatment of any of the particular indications set forth hereinabove in a subject in need thereof which comprises administering a therapeutically effective amount of an agent of the invention;

(4) A method for treating or preventing a disease or condition in which vanilloid receptor plays a role or is implicated comprising administering to a mammal in need thereof a therapeutically effective amount of an agent of the invention;

(5) Use of an agent of the invention for the manufacture of a medicament for the treatment or prevention of a disease or condition in which activity of vanilloid receptor plays a role or is implicated;

(6) A method as set forth hereinabove comprising co-administration, e. g., concomitantly or in sequence, of a therapeutically effective amount of a vanilloid receptor antagonist, e. g., an agent of the invention and a second drug substance, said second drug substance being, e. g., for use in any of the particular indications set forth hereinabove; and (7) A combination comprising a therapeutically effective amount of an agent of the invention and a second drug substance, said second drug substance being, e. g., for use in any of the particular indications set forth hereinabove.

EXAMPLES

In the Examples which follow, which are not intended to limit, in any way, the scope of the present invention, the following abbreviations are used:

| | |
|---|---|
| eq. | equivalent(s) |
| h | hour(s) |
| min | minute(s) |

The HPLC retention time (RT) data correspond to the following conditions: Phenomenex Luna reversed phase C18 3 micron (30×4.6 mm) column; column temperature 25° C.; gradient elution 10% MeCN in water (+0.08% formic acid) to 100% MeCN over 10 minutes (rate=3.0 ml/minute). The purity values are quoted at 254 nm.

Example 1

2-(4-Chlorophenyl)-1-(3,4-difluoro-2-hydroxy-phenyl)-ethanone

A mixture of aluminium chloride (7.66 g, 57.4 mmol, 1.5 eq.) and (4-chlorophenyl)acetyl chloride (8.7 g, 46 mmol, 1.2 eq.) in 1,2-dichloroethane (75 ml) is stirred at 0° C. for 30 min. A solution of 2,3-difluorophenol (5 g, 38.4 mmol) in 1,2-dichloroethane (25 ml) is added to the reaction mixture, which is heated in an oil bath at 90° C. overnight. The reaction mixture is cooled to room temperature, diluted with water and extracted with ethyl acetate. The organic phase is dried over anhydrous magnesium sulfate, filtered and evaporated to dryness in vacuo to afford a brown solid. This is triturated with hexane/ethyl acetate (9:1), filtered and dried to afford the title compound as a pale brown fine solid which is 87% pure by HPLC analysis.

Isobutyric acid 6-[2-(4-chlorophenyl)acetyl]-2,3-difluorophenyl ester

A solution of 2-(4-chlorophenyl)-1-(3,4-difluoro-2-hydroxy-phenyl)-ethanone (4.5 g, 87% pure, 13.85 mmol) and triethylamine (1.7 g, 2.35 ml, 16.8 mmol, 1.2 eq.) in methylene chloride (100 ml) is treated dropwise at ambient temperature with isobutyryl chloride (1.79 g, 1.76 ml, 16.8 mmol, 1.2 eq.). After stirring for 5 h, the solution is washed successively with 2M HCl solution and saturated sodium hydrogen carbonate solution. The organic phase is dried over anhydrous magnesium sulphate, filtered and evaporated to dryness in vacuo to afford a black residue. This is triturated with methanol at room temperature overnight to afford a brown solid, which is filtered and washed with methanol. The solid is purified twice by flash chromatography (ethyl acetate/cyclohexane=1:9) to furnish the title compound.

2-(4-Chlorophenyl)-1-(3,4-difluoro-2-hydroxy-phenyl)-4-methyl-pentane-1,3-dione Sodium hydride (1.5 g, 37.5 mmol, 60% dispersion in mineral oil, 4 eq.) is added portionwise to a stirred solution of isobutyric acid 6-[2-(4-chlorophenyl)acetyl]-2,3-difluorophenyl ester (3.16 g, 8.97 mmol) in tetrahydrofuran (60 ml) over 15 min. The mixture is heated in an oil bath at 80° C. for 4 h. The reaction is cooled to room temperature, diluted with 2M HCl solution and washed with ethyl acetate. The organic phase is dried over anhydrous magnesium sulfate, filtered, and concentrated in vacuo to afford the title compound as a brown oil. The product is used in the next step without further purification.

3-(4-Chlorophenyl)-7,8-difluoro-2-isopropyl-chromen-4-one

A mixture of 2-(4-chlorophenyl)-1-(3,4-difluoro-2-hydroxy-phenyl)-4-methyl-pentane-1,3-dione (3.65 g, 10.3 mmol) in acetic acid (36 ml) and concentrated HCl solution (2 ml) is stirred at 140° C. for 3 h. The reaction mixture is cooled to room temperature, poured onto ice-water and extracted with methylene chloride. The organic layer is washed with saturated sodium hydrogen carbonate solution, dried over anhydrous magnesium sulfate and evaporated to dryness in vacuo to afford the title compound as a brown solid.

3-(4-Chlorophenyl)-8-fluoro-7-(2-hydroxyethylamino)-2-isopropyl-chromen-4-one A stirred solution of 3-(4-chlorophenyl)-7,8-difluoro-2-isopropyl-chromen-4-one (3.94 g, 11.8 mmol), triethylamine (2.4 g, 3.2 ml, 23.6 mmol, 2 eq.) and ethanolamine (0.72 g, 0.71 ml, 11.8 mmol, 1 eq.) in N,N-dimethylacetamide (200 ml) is heated at 150° C. overnight. The reaction mixture is allowed to cool to room temperature and the solvent is removed by evaporation in vacuo. The residue is dissolved in ethyl acetate and washed with 2M HCl solution. The organic layer is washed with brine, dried over anhydrous magnesium sulfate, filtered and evaporated to dryness in vacuo to afford a brown oil. The oil is purified by flash chromatography (cyclohexane/ethyl acetate=9:1 to 4:6) to afford the title compound.

7-(4-Chlorophenyl)-6-isopropyl-2,3-dihydro-1H-1-aza-4,5-dioxa-phenanthren-8-one To a solution of 3-(4-chlorophenyl)-8-fluoro-7-(2-hydroxyethylamino)-2-isopropyl-chromen-4-one (0.195 g, 0.52 mmol) in dimethylformamide (5 ml) is added sodium hydride (0.053 g, 1.32 mmol, 60% dispersion in mineral oil, 2.55 eq.). The mixture is irradiated in a microwave instrument at 150° C. for 70 min. The solvent is removed by evaporation in vacuo to afford a brown oil. This is dissolved in hot ethyl acetate and allowed to cool to room temperature, whereupon a brown solid precipitates. More product can be recovered from the mother liquor by flash chromatography (cyclohexane/ethyl acetate=9:1). The solid products are combined and dried at 60° C. overnight under high vacuum to afford the title compound.

356.21, $(M+H)^+$, 100%. $^1$H NMR (400 MHz, DMSO-$d_6$): 7.48 (2H, dd, J=1.9, 6.5 Hz), 7.35 (1H, d, J=8.7 Hz), 7.25 (2H, dd, J=2, 6.5 Hz), 6.86 (1H, br s), 6.68 (1H, d, J=8.7 Hz), 4.29-4.23 (2H, m), 3.5-3.4 (2H, m), 2.76 (1H, m), 1.19 (6H, d, J=6.9 Hz). RT=5.43 min (100%).

Example 1a

In a manner analogous to that described in Example 1, the following compounds can also be prepared:

(a) 7-(4-Chlorophenyl)-6-isopropyl-3-methyl-2,3-dihydro-1H-1-aza-4,5-dioxa-phenanthren-8-one 370, $(M+H)^+$. $^1$H NMR (400 MHz, DMSO-$d_6$): 7.48 (2H, d, J=8.4 Hz), 7.34 (1H, d, J=8.7 Hz), 7.25 (2H, d, J=8.4 Hz), 6.87 (1H, brs), 6.68 (1H, d, J=8.6 Hz), 4.2 (1H, m), 3.48 (1H, m), 3.07 (1H, m), 2.76 (1H, m), 1.37 (3H, d, J=6.3 Hz), 1.19 (6H, d, J=6.9 Hz). RT=6.030 min, purity=100%.

(b) (R)-7-(4-Chlorophenyl)-6-isopropyl-3-methyl-2,3-dihydro-1H-1-aza-4,5-dioxa-phenanthren-8-one (using enantiomerically pure building blocks)

370, $(M+H)^+$. $^1$H NMR (400 MHz, DMSO-$d_6$): 7.48 (2H, d, J=8.4 Hz), 7.34 (1H, d, J=8.7 Hz), 7.25 (2H, d, J=8.4 Hz), 6.87 (1H, brs), 6.68 (1H, d, J=8.6 Hz), 4.2 (1H, m), 3.48 (1H, m), 3.07 (1H, m), 2.76 (1H, m), 1.37 (3H, d, J=6.3 Hz), 1.19 (6H, d, J=6.9 Hz). RT=6.021 min, purity=100%.

(c) (S)-7-(4-Chlorophenyl)-6-isopropyl-3-methyl-2,3-dihydro-1H-1-aza-4,5-dioxa-phenanthren-8-one (using enantiomerically pure building blocks)

370, $(M+H)^+$. $^1$H NMR (400 MHz, DMSO-$d_6$): 7.48 (2H, d, J=8.4 Hz), 7.34 (1H, d, J=8.7 Hz), 7.25 (2H, d, J=8.4 Hz), 6.87 (1H, br s), 6.68 (1H, d, J=8.6 Hz), 4.2 (1H, m), 3.48 (1H, m), 3.07 (1H, m), 2.76 (1H, m), 1.37 (3H, d, J=6.3 Hz), 1.19 (6H, d, J=6.9 Hz). RT=6.028 min, purity=100%.

Example 2

7-Benzyloxy-3-(4-chlorophenyl)-2-isopropyl-4-oxo-4H-chromene-8-carbaldehyde

To a solution of 3-(4-chlorophenyl)-7-hydroxy-2-isopropyl-4-oxo-4H-chromene-8-carbaldehyde (7.95 g, 23.2 mmol) and benzyl bromide (7.93 g, 46.4 mmol) in N,N-dimethylformamide (200 ml) is added $K_2CO_3$ (9.61 g, 69.5 mmol), and the reaction mixture is stirred at room temperature for 96 h. The mixture is poured into ice/water, extracted with $CH_2Cl_2$, dried ($MgSO_4$) and concentrated in vacuo. The resulting solid residue is stirred with hexane/ethyl acetate for 1 h, the solvent is decanted, and the solid is stirred with hexane/diethyl ether for 16 h. The title compound is collected by filtration and washed with hexane to afford a pale brown solid.

7-Benzyloxy-3-(4-chlorophenyl)-8-hydroxy-2-isopropyl-chromen-4-one

To a solution of 7-benzyloxy-3-(4-chlorophenyl)-2-isopropyl-4-oxo-4H-chromene-8-carbaldehyde (8.03 g, 18.6 mmol) in $CH_2Cl_2$ (200 ml) is added m-chloroperbenzoic acid (9.24 g, 53.5 mmol). The reaction mixture is stirred at 50° C. for 4 h, washed with saturated $NaHCO_3$ solution, dried ($MgSO_4$) and concentrated in vacuo to give a yellow oil. To a solution of the oil in methanol (350 ml) is added aqueous KOH solution (10%, 35 ml), and the mixture is stirred at room temperature overnight. The mixture is concentrated to a ca. 50 ml volume, ice/water is added, and the mixture is acidified with concentrated HCl. A solid is isolated by filtration, washed with water and taken up into $CH_2Cl_2$. The $CH_2Cl_2$ solution is dried ($MgSO_4$), and the solvent is removed in vacuo to afford a dark brown solid. This is stirred in hot hexane/ethyl acetate and filtered to afford the title compound as a colourless solid. A further crop of the desired product can be isolated from the filtrate by concentrating the hot solution to a quarter of its original volume and allowing it to stand at room temperature.

7-Benzyloxy-3-(4-chlorophenyl)-2-isopropyl-8-methoxy-chromen-4-one

To a solution of 7-benzyloxy-3-(4-chlorophenyl)-8-hydroxy-2-isopropyl-chromen-4-one (3.01 g, 7.15 mmol) and iodomethane (1.17 g, 8.22 mmol) in N,N-dimethylformamide (60 ml) is added $K_2CO_3$ (1.98 g, 14.3 mmol). The reaction mixture is stirred at room temperature for 72 h. The mixture is diluted with ethyl acetate and water, and the organic phase is washed with sodium thiosulfate solution and brine, dried ($MgSO_4$) and concentrated in vacuo. The resulting off-white solid residue is triturated with ethyl acetate to afford the title compound as a white solid.

3-(4-Chlorophenyl)-7-hydroxy-2-isopropyl-8-methoxy-chromen-4-one

A suspension of 7-benzyloxy-3-(4-chlorophenyl)-2-isopropyl-8-methoxy-chromen-4-one (2.68 g, 6.16 mmol) and Pd/carbon (20%, 268 mg) in tetrahydrofuran (30 ml), absolute ethanol (30 ml) and 5M HCl solution (15 ml) is stirred under a balloon of $H_2$ at room temperature for 3 h. The reaction mixture is filtered through a pad of Celite filter aid, which is itself washed with tetrahydrofuran. The solvent is removed under reduced pressure to afford the desired product, which is used without further purification.

Trifluoromethanesulfonic acid 3-(4-chlorophenyl)-2-isopropyl-8-methoxy-4-oxo-4H-chromen-7-yl ester A solution of trifluoromethanesulfonic acid anhydride (3.5 g, 2.1 ml, 12.4 mmol, 2 eq.) in anhydrous methylene chloride (10 ml) is added dropwise to a stirred solution of sodium 3-(4-chlorophenyl)-2-isopropyl-8-methoxy-4-oxo-4H-chromen-7-olate (2.28 g, 6.22 mmol; prepared by treating 3-(4-chlorophenyl)-7-hydroxy-2-isopropyl-8-methoxy-chromen-4-one with a molar equivalent of sodium hydride in dry tetrahydrofuran), pyridine (2 g, 2.1 ml, 25.5 mmol, 4.1 eq.) and 4-dimethylaminopyridine (0.076 g, 0.62 mmol, 0.1 eq.) in anhydrous methylene chloride (60 ml) at 0° C. After stirring overnight, the solution is washed with 1M HCl solution. The organic phase is dried over anhydrous magnesium sulfate and filtered, and the solvent is removed by evaporation in vacuo to afford the title compound as a brown foam. The product is used in the next step without further purification.

7-Amino-3-(4-chlorophenyl)-2-isopropyl-8-methoxy-chromen-4-one

A stirred mixture of trifluoromethanesulfonic acid 3-(4-chlorophenyl)-2-isopropyl-8-methoxy-4-oxo-4H-chromen-7-yl ester (2.41 g, 5.05 mmol), 1,1'-bis(diphenylphosphino)-ferrocene (5.6 g, 10.1 mmol, 2 eq.), tris(dibenzylideneacetone)dipalladium (0) (3.08 g, 3.36 mmol, 0.665 eq.), sodium t-butoxide (0.58 g, 6.06 mmol, 1.2 eq.) and benzophenone-imine (1.1 g, 1.02 ml, 6.06 mmol, 1.2 eq.) in toluene (160 ml) is heated under reflux at 130° C. for 45 min. The reaction mixture is allowed to cool to room temperature and filtered through a pad of Celite filter aid. The Celite is washed with methylene chloride, and the filtrate is evaporated to dryness in vacuo to afford 7-(benzhydrylideneamino)-3-(4-chlorophenyl)-2-isopropyl-8-methoxy-chromen-4-one as a red oil. A stirred solution of the red oil in tetrahydrofuran (80 ml) is treated with 2M HCl solution (80 ml). After 30 min, the reaction mixture is basified with 17% ammonia solution and washed with ethyl acetate. The organic layer is dried over anhydrous magnesium sulfate and filtered, and the solvent is removed by evaporation in vacuo to afford a dark residue. This is purified by flash chromatography (cyclohexane/ethyl acetate=9:1) to afford the title compound.

7-Amino-3-(4-chlorophenyl)-8-hydroxy-2-isopropyl-chromen-4-one

A stirred solution of 7-amino-3-(4-chlorophenyl)-2-isopropyl-8-methoxy-chromen-4-one (0.178 g, 0.52 mmol) in methylene chloride (5 ml) under an argon atmosphere is cooled to −78° C. and treated with boron tribromide (1M solution in methylene chloride, 3.2 ml, 3.2 mmol, 6.2 eq.). The reaction mixture is stirred at −78° C. for 1 h and at room temperature for 45 min, whereupon HPLC analysis indicates that the reaction is complete. The reaction mixture is treated with water (32 ml) and stirred at ambient temperature overnight. The mixture is washed with methylene chloride, and the organic layer is washed with 5% sodium thiosulfate solution, followed by brine. The organic phase is dried over anhydrous magnesium sulfate and filtered, and the solvent is removed by evaporation in vacuo to afford a brown oil. The oil is purified by flash chromatography (hexane/ethyl acetate=9:1 through 1% methanol in ethyl acetate to methylene chloride/methanol=9:1) to afford the title compound.

7-(4-Chlorophenyl)-8-isopropyl-3H-chromeno[7,8-d]oxazole-2,6-dione

A stirred solution of 7-amino-3-(4-chlorophenyl)-8-hydroxy-2-isopropyl-chromen-4-one (0.0532 g, 0.16 mmol) in anhydrous methylene chloride (2 ml) is treated at room temperature with a 20% phosgene in toluene solution (0.08 ml). After 30 min, triethylamine (0.032 g, 0.045 ml, 0.32 mmol, 2 eq.) is added, and the reaction mixture is stirred at room temperature for 1 h, transferred to the head of an aminoalkylated silica gel column (Sepra $NH_2$, 50 micrometer, Phenomenex) and purified by flash chromatography (cyclohexane/ethyl acetate=9:1 to 1% acetic acid in ethyl acetate) to afford the title compound.

355.972, $M^+$. $^1H$ NMR (400 MHz, DMSO-$d_6$): 12.4 (1H, br s), 7.89 (1H, d, J=8.4 Hz), 7.57 (2H, dd, J=1.8, 6.5 Hz), 7.36 (2H, dd, J=1.9, 6.6 Hz), 7.29 (1H, d, J=8.4 Hz), 2.86 (1H, m), 1.29 (6H, d, J=6.9 Hz). RT=5.160 min, purity=100%.

Example 2a

In a manner analogous to that described in Example 2, the following compound can also be prepared:

7-(4-Chlorophenyl)-6-isopropyl-8-oxo-2,3-dihydro-8H-4,5-dioxa-1-aza-phenanthrene-1-carbaldehyde 384.21, $(M+H)^+$. $^1H$ NMR (400 MHz, DMSO-$d_6$, major rotamer): 9.13 (1H, s), 7.71 (1H, d, J=9 Hz), 7.55-7.50 (3H, m), 7.30-7.28 (2H, d, J=8.4 Hz), 4.44-4.42 (2H, apparent t), 3.94-3.92 (2H, apparent t), 2.81 (1H, quin, J=6.7 Hz), 1.22-1.21 (6H, d, J=6.8 Hz). RT=5.330 min, purity=98.4%.

Example 3

N-[3-(4-Chlorophenyl)-8-hydroxy-2-isopropyl-4-oxo-4H-chromen-7-yl]formamide

A stirred mixture of 7-amino-3-(4-chlorophenyl)-8-hydroxy-2-isopropyl-chromen-4-one (1.1 g, 3.35 mmol) and sodium formate (0.23 g, 3.35 mmol) in formic acid (50 ml) is heated under reflux for 2 h. After cooling to room temperature, the reaction mixture is poured into ice/water (300 ml) with stirring. The resulting aqueous suspension is washed with ethyl acetate (2×100 ml). The combined organic layers are washed with water (3×100 ml) and brine (100 ml), dried (magnesium sulfate) and filtered. The solvent is removed by evaporation in vacuo to afford a dark brown oil. This is purified by flash chromatography (hexane/ethyl acetate=1:1, followed by 100% ethyl acetate) to afford the title compound.

3-(4-Chlorophenyl)-2-isopropyl-4-oxo-9,10-dihydro-4H,8H-1,11-dioxa-7-aza-cyclohepta[a]naphthalene-7-carbaldehyde A stirred mixture of N-[3-(4-chlorophenyl)-8-hydroxy-2-isopropyl-4-oxo-4H-chromen-7-yl]formamide (0.122 g, 0.34 mmol), cesium carbonate (0.444 g, 1.36 mmol, 4 eq.) and 1,3-dibromopropane (0.069 g, 0.34 mmol) in anhydrous N,N-dimethylformamide (3 ml) is heated at 60° C. under a nitrogen atmosphere for 2 h. The mixture is cooled to room temperature and filtered through Celite filter aid. The pad of Celite is washed with ethyl acetate and methylene chloride, and the combined filtrates are evaporated in vacuo to afford a brown solid. This is purified by flash chromatography (cyclohexane/ethyl acetate=9:1 to 4:1) to furnish the title compound as a yellow solid.

3-(4-Chlorophenyl)-2-isopropyl-7,8,9,10-tetrahydro-1,11-dioxa-7-aza-cyclohepta[a]naphthalene-4-one A stirred mixture of 3-(4-chlorophenyl)-2-isopropyl-4-oxo-9,10-dihydro-4H,8H-1,11-dioxa-7-aza-cyclohepta[a]naphthalene-7-carbaldehyde (0.063 g, 0.158 mmol) in 1M HCl solution (4 ml) and methanol (6 ml) is heated under reflux for 1 h under a nitrogen atmosphere. The mixture is allowed to cool to room temperature, and the methanol solvent is removed by evaporation in vacuo. The concentrated mixture is diluted with water (5 ml) and treated with solid sodium hydrogen carbonate, until a pH of 7-8 is attained. The mixture is washed successively with ethyl acetate and methylene chloride. The combined organic phases are dried (magnesium sulfate) and filtered, and the solvent is removed by evaporation in vacuo to afford a crude orange solid. This is stirred overnight in a solution of 2M HCl in diethyl ether (3 ml), filtered and dried at room temperature under high vacuum to give the title compound as a cream-coloured solid.

370, (M+H)$^+$. $^1$H NMR (400 MHz, DMSO-d$_6$): 7.48 (2H, d, J=8.3 Hz), 7.42 (1H, d, J=8.7 Hz), 7.25 (2H, d, J=8.3 Hz), 6.8 (1H, d, J=8.7 Hz), 4.3-4.2 (2H, t, J=5.8 Hz), 3.4-3.3 (2H, m), 2.76 (1H, m), 2.1-1.95 (2H, m), 1.2 (6H, d, J=6.9 Hz) RT=5.849 min, purity=92.8%.

Example 3a

In a manner analogous to that described in Example 3, the following compound can also be prepared:

7-(4-Chlorophenyl)-2-hydroxymethyl-6-isopropyl-2,3-dihydro-1H-4,5-dioxa-1-aza-phenanthren-8-one 386, (M+H)$^+$. $^1$H NMR (400 MHz, DMSO-d$_6$): 7.46 (2H, d, J=8.4 Hz), 7.34 (1H, d, J=8.7 Hz), 7.22 (2H, d, J=8.4 Hz), 6.96 (1H, br s), 6.7 (1H, d, J=8.7 Hz), 5.01 (1H, t), 4.17 (2H, m), 3.55-3.4 (3H, m), 2.75 (1H, s), 1.19 (6H, d, J=6.9 Hz). RT=4.585 min, purity=97.55%.

Example 4

Trifluoromethanesulfonic acid 3-(4-chlorophenyl)-2-isopropyl-4-oxo-4H-chromen-7-yl ester A mixture of 3-(4-chlorophenyl)-7-hydroxy-2-isopropyl-chromen-4-one (5.11 g, 16.2 mmol), 4-dimethylaminopyridine (0.198 g, 1.62 mmol) and pyridine (5.5 g, 70 mmol) in anhydrous CH$_2$Cl$_2$ (170 ml) is cooled in an ice bath. A solution of trifluoromethanesulfonic acid anhydride (9.0 g, 32 mmol) in anhydrous CH$_2$Cl$_2$ (10 ml) is added dropwise to the cooled mixture, which is allowed to warm to room temperature over 3 hours. 1M HCl solution (150 ml) is added, the resultant mixture is stirred for 10 minutes, and the two phases are separated. The aqueous phase is washed with CH$_2$Cl$_2$ (3×). The organic phases are combined and dried (MgSO$_4$), and the solvent is removed under reduced pressure. The resulting red oil is dried in vacuo to afford the desired compound as a pink foam.

7-(Benzhydrylideneamino)-3-(4-chlorophenyl)-2-isopropyl-chromen-4-one

A mixture of trifluoromethanesulfonic acid 3-(4-chlorophenyl)-2-isopropyl-4-oxo-4H-chromen-7-yl ester (6.96 g, 15.6 mmol), palladium acetate (0.35 g, 1.56 mmol), cesium carbonate (12.7 g, 38.9 mmol) and racemic 2,2'-bis(diphenylphosphino)-1,1'-binaphthyl (BINAP; 0.97 g, 1.56 mmol) in anhydrous tetrahydrofuran (230 ml) under an atmosphere of nitrogen is treated with benzophenone imine (3.66 g, 20.2 mmol) and allowed to stir at 80° C. for 22 hours. After allowing the resultant mixture to stir at room temperature for an additional 24 hours, it is diluted with water (300 ml) and extracted with ethyl acetate (3×300 ml). The organic extracts are combined, washed with brine, dried (MgSO4), filtered, concentrated in vacuo and purified by flash chromatography over silica gel (10% ethyl acetate/cyclohexane) to afford the desired compound as a dark yellow solid.

7-Amino-3-(4-chlorophenyl)-2-isopropyl-chromen-4-one

A solution of 7-(benzhydrylideneamino)-3-(4-chlorophenyl)-2-isopropyl-chromen-4-one (5.72 g, 12 mmol) in tetrahydrofuran (150 ml) is treated with 2M HCl solution (150 ml) and allowed to stir at room temperature for 1 hour. The solution is basified with 17% ammonia solution (150 ml), and the mixture is extracted with ethyl acetate (3×200 ml). The organic extracts are combined, dried (MgSO$_4$), filtered and concentrated to afford a yellow suspension. The suspension is triturated with hexanes to afford the title compound as a pale yellow solid, which is isolated by filtration and dried in vacuo overnight.

7-Amino-8-bromo-3-(4-chlorophenyl)-2-isopropyl-chromen-4-one

A stirred solution of 7-amino-3-(4-chlorophenyl)-2-isopropyl-chromen-4-one (0.36 g, 1.15 mmol) in chloroform (10 ml) is treated at room temperature with N-bromosuccinimide (0.21 g, 1.2 mmol, 1.05 eq.). After stirring for 20 min, the mixture is partitioned between water (150 ml) and ethyl acetate (50 ml). The organic phase is washed with brine (100 ml), dried (magnesium sulfate) and filtered, and the solvent is removed by evaporation in vacuo to afford the title compound as an orange solid. The product is used in the next step without further purification.

[8-Bromo-3-(4-chlorophenyl)-2-isopropyl-4-oxo-4H-chromen-7-yl]carbamic acid benzyl ester A stirred solution of 7-amino-8-bromo-3-(4-chlorophenyl)-2-isopropyl-chromen-4-one (0.242 g, 0.62 mmol) in anhydrous methylene chloride (5 ml) is treated with a 20% solution of phosgene in toluene (0.5 ml). After 3 h, triethylamine (0.12 g, 0.17 ml, 1.24 mmol, 2 eq.) is added, followed by benzyl alcohol (0.067 g, 0.064 ml, 0.62 mmol), and the solution is stirred at room temperature overnight. The solution is diluted with methylene chloride and washed with water. The organic layer is dried (magnesium sulfate) and filtered, and the solvent is removed by evaporation in vacuo. The resulting solid is purified by flash chromatography (cyclohexane/ethyl acetate=9:1) to afford the title compound as a pale yellow solid.

Allyl-[8-bromo-3-(4-chlorophenyl)-2-isopropyl-4-oxo-4H-chromen-7-yl]carbamic acid benzyl ester A mixture of [8-bromo-3-(4-chlorophenyl)-2-isopropyl-4-oxo-4H-chromen-7-yl]carbamic acid benzyl ester (0.231 g, 0.44 mmol) and cesium carbonate (0.228 g, 0.701 mmol, 1.6 eq.) in N,N-dimethylformamide (10 ml) is treated with allyl bromide (0.058 g, 0.042 ml, 0.48 mmol, 1.1 eq.), and the mixture is stirred at room temperature for 4 h. The mixture is diluted with water and washed twice with ethyl acetate. The aqueous phase is additionally washed with methylene chloride. The combined organic phases are dried (magnesium sulfate) and filtered and the solvent is removed by evaporation in vacuo to afford the title compound as a yellow solid. The product is used in the next step without further purification.

3-(4-Chlorophenyl)-2-isopropyl-9-methyl-4-oxo-4H-pyrano[2,3-e]indole-7-carboxylic acid benzyl ester A mixture of allyl-[8-bromo-3-(4-chlorophenyl)-2-isopropyl-4-oxo-4H-chromen-7-yl]carbamic acid benzyl ester (0.094 g, 0.166 mmol), tetrakis(triphenylphosphine)palladium (0) (0.01 g, 0.0086 mmol, 5 mol %) and cesium carbonate (0.27 g, 0.83 mmol, 5 eq.) in acetonitrile (4 ml) and methylene chloride (1 ml) is irradiated in a microwave instrument at 100° C. for 20 min. The mixture is filtered through Celite filter aid, and the pad of Celite is washed with methylene chloride, followed by ethyl acetate. The combined filtrates are evaporated in vacuo, and the residue is purified by flash chromatography (15% ethyl acetate in cyclohexane) to afford a yellow solid. LC-MS analysis suggests, that the product is a mixture of carbon-carbon double bond isomers in a 1.7:1 ratio.

3-(4-Chlorophenyl)-2-isopropyl-9-methyl-7H-pyrano[2,3-e]indol-4-one

A stirred suspension of 3-(4-chlorophenyl)-2-isopropyl-9-methyl-4-oxo-4H-pyrano[2,3-e]indole-7-carboxylic acid benzyl ester and its positional isomer (0.063 g, 0.13 mmol) and 20% Pd on activated carbon (0.013 g) in tetrahydrofuran (1.5 ml), ethanol (1.5 ml) and 5M HCl solution (0.75 ml) is stirred under a hydrogen atmosphere for 3.5 h at room temperature. The catalyst is removed by filtration through Celite filter aid, and the pad of Celite is washed with ethyl acetate and methylene chloride. The combined filtrates are evaporated in vacuo, and the residue is purified by flash chromatography (cyclohexane/ethyl acetate=9:1 to 5:1) to afford the title compound as a pale orange solid.

352, (M+H)+. $^1$H NMR (400 MHz, DMSO-$d_6$): 11.48 (1H, br s), 7.64 (1H, d, J=8.7 Hz), 7.48 (2H, d, J=8.4 Hz), 7.37 (1H, d, J=8.7 Hz), 7.29 (2H, d, J=8.4 Hz), 7.25 (1H, s), 2.85 (1H, m), 2.59 (3H, s), 1.28 (6H, d, J=6.9 Hz). RT=6.307 min, purity=100%.

Example 5

1-[2-Hydroxy-4-(4-methoxy-benzyloxy)-phenyl] ethanone

2',4'-Dihydroxyacetophenone (11.71 g, 0.077 mol), 4-methoxybenzyl chloride (10.44 ml, 0.077 mol), anhydrous potassium carbonate (11.75 g, 0.085 mol) and potassium iodide (12.78 g, 0.077 mol) are heated together in refluxing dry acetone (80 ml) for 4 hours. The mixture is then cooled to room temperature, poured into water (250 ml) and extracted with ethyl acetate (3×100 ml). The ethyl acetate extracts are combined, washed with saturated brine (100 ml), dried (MgSO$_4$), filtered and concentrated, until crystallization commences. After standing at 4° C. for 16 h, the crystals are recovered by filtration, washed with cold ethyl acetate and then with n-hexane and dried.

Isobutyric acid 2-acetyl-5-(4-methoxy-benzyloxy)-phenyl ester

1-[2-Hydroxy-4-(4-methoxy-benzyloxy)-phenyl]-ethanone (9.11 g, 0.034 mol) is dissolved in dry dichloromethane (120 ml) under an atmosphere of dry argon. Triethylamine (5.14 ml, 0.037 mol) and 4-dimethylaminopyridine (0.204 g, 1.67 mmol) are added, and the mixture is cooled to 0° C. using an ice-water bath. Isobutyryl chloride (3.89 ml, 0.037 mol) is then added dropwise, and the mixture is stirred while warming to room temperature. The mixture is poured into water (100 ml), and the dichloromethane layer is separated, washed with saturated brine (100 ml), dried (MgSO$_4$), treated with activated charcoal (300 mg), filtered and evaporated to give a pale pink solid.

1-Hydroxy-1-[2-hydroxy-4-(4-methoxy-benzyloxy)-phenyl]-4-methyl-pent-1-en-3-one (and keto tautomer)

To a solution of isobutyric acid 2-acetyl-5-(4-methoxybenzyloxy)-phenyl ester (11.45 g, 0.033 mol) in dry tetrahydrofuran (160 ml) is added, portionwise over ca. 15 minutes at room temperature, sodium hydride (60% dispersion in mineral oil, 4.68 g, 0.117 mol). The reaction mixture is stirred at room temperature for two hours, during which there is a slight exotherm (the mixture reaches ca. 40° C.). Aqueous 5% ammonium hydroxide (100 ml) is carefully added to quench the reaction, and then the mixture is poured into water (200 ml) and extracted with ethyl acetate (3×75 ml). The ethyl acetate extracts are combined, washed with saturated brine (100 ml), dried (Na$_2$SO$_4$), filtered and concentrated under reduced pressure until crystallization commences. After standing at 4° C. for 16 h, the crystals are recovered by filtration, washed with n-hexane and dried.

1-[2-(tert-Butyl-dimethyl-silanyloxy)-4-(4-methoxy-benzyloxy)-phenyl]-1-hydroxy-4-methyl-pent-1-en-3-one (and keto tautomer)

1-Hydroxy-1-[2-hydroxy-4-(4-methoxy-benzyloxy)-phenyl]-4-methyl-pent-1-en-3-one (4.75 g, 13.9 mmol), t-butyldimethylsilylchloride (2.3 g, 15.3 mmol), imidazole (1.04 g, 15.3 mmol) and 4-dimethylaminopyridine (0.17 g, 1.4 mmol) are mixed together in dry N,N-dimethylformamide (100 ml) at room temperature under argon for 60 hours. The mixture is poured into water (300 ml) and extracted with diethyl ether (3×100 ml). The ether extracts are combined, washed with saturated brine (100 ml), dried ($MgSO_4$), filtered and evaporated to give a cream coloured solid. This is recrystallised from hot n-hexane to give a colourless crystalline solid. Additional product can be obtained by chromatography (silica gel) of the residues from the mother liquor using cyclohexane and cyclohexane/ethyl acetate (4:1) as eluant.

2-Bromo-1-[2-(tert-butyl-dimethyl-silanyloxy)-4-(4-methoxy-benzyloxy)-phenyl]-4-methyl-pentane-1,3-dione 1-[2-(tert-Butyl-dimethyl-silanyloxy)-4-(4-methoxy-benzyloxy)-phenyl]-1-hydroxy-4-methyl-pent-1-en-3-one (5.81 g, 12.72 mmol) is dissolved in dry dichloromethane (100 ml) at room temperature. N-bromosuccinimide (2.38 g, 13.36 mmol) is added portionwise. The reaction mixture is stirred at room temperature for 30 minutes, poured into water (200 ml) and extracted with dichloromethane (3×75 ml). The dichloromethane extracts are combined, washed with saturated brine (100 ml), dried ($MgSO_4$), filtered and evaporated to give a pale yellow solid.

3-Bromo-7-hydroxy-2-isopropyl-chromen-4-one

2-Bromo-1-[2-(tert-butyl-dimethyl-silanyloxy)-4-(4-methoxy-benzyloxy)-phenyl]-4-methyl-pentane-1,3-dione (6.77 g, 12.65 mmol) is dissolved in absolute ethanol (350 ml) at 50° C. Concentrated sulfuric acid (16 ml) is added dropwise. The mixture is stirred at 50° C. for 16 hours, after which time further 0.5 ml of concentrated sulfuric acid are added. The stirring is continued for a further 4 hours at 50° C. The reaction mixture is cooled to room temperature, and most of the ethanol is removed under reduced pressure. Water (400 ml) is added to the residue, and the colourless solid formed is recovered by filtration and dried in a desiccator. This material is not pure enough for subsequent use, so it is partitioned between water and ethyl acetate and extracted with ethyl acetate (3×100 ml). The ethyl acetate extracts are combined, washed with saturated brine (100 ml), dried ($MgSO_4$), treated with activated charcoal (300 mg), filtered and concentrated, until crystallization commences. After standing at 4° C. for 16 h, the crystals are recovered by filtration, washed with n-hexane and dried.

3-Bromo-7-hydroxy-2-isopropyl-8-nitro-chromen-4-one

3-Bromo-7-hydroxy-2-isopropyl-chromen-4-one (778 mg, 2.75 mmol) is dissolved in concentrated sulphuric acid (4 ml), and the solution is cooled to 0° C. A solution of fuming nitric acid (189 mg, 3 mmol) in concentrated sulphuric acid (1 ml) is added dropwise. The mixture is stirred at 0° C. for 30 min, poured onto ice, recovered by filtration and dried to give a cream-coloured solid.

2,4,6-Trimethyl-benzenesulfonic acid 3-bromo-2-isopropyl-8-nitro-4-oxo-4H-chromen-7-yl ester 3-Bromo-7-hydroxy-2-isopropyl-8-nitro-chromen-4-one (4.38 g, 13.35 mmol) is dissolved in dry dichloromethane (100 ml) at room temperature. Triethylamine (1.96 ml, 14.03 mmol) and 2-(mesitylene)sulfonyl chloride (3.07 g, 14.03 mmol) are added, and the reaction mixture is stirred at room temperature for 1 day. The reaction mixture is then quenched with saturated ammonium chloride solution (60 ml), and water (40 ml) is added. The dichloromethane layer is separated, and the aqueous phase is further extracted with dichloromethane (2×60 ml). The dichloromethane extracts are combined, washed with saturated brine (60 ml), dried ($MgSO_4$), filtered and evaporated to give a yellow solid. This is triturated with diethyl ether/dichloromethane, and the mixture is filtered to give a pale yellow powder.

3-Bromo-2-isopropyl-7-(4-methoxybenzylamino)-8-nitro-chromen-4-one

To a solution of 2,4,6-trimethyl-benzenesulfonic acid 3-bromo-2-isopropyl-8-nitro-4-oxo-4H-chromen-7-yl ester (1.906 g, 3.5 mmol) in dry toluene (18 ml) in a 20 ml capacity microwave tube is added p-methoxybenzylamine (0.69 ml, 5.26 mmol). The mixture is heated at 130° C. under microwave irradiation for 90 minutes and then at 140° C. under microwave irradiation for a further 30 minutes. Water (40 ml) is added, and the mixture is extracted with ethyl acetate (3×100 ml). The ethyl acetate extracts are combined, washed with saturated brine (50 ml), dried ($MgSO_4$), filtered and evaporated. The crude product is purified by chromatography on silica gel using cyclohexane-ethyl acetate (8:1) as eluant. The product-containing fractions are evaporated under reduced pressure, and the residue is triturated with diethyl ether to give a pale yellow solid.

3-(4-Chlorophenyl)-2-isopropyl-7-(4-methoxybenzylamino)-8-nitro-chromen-4-one 3-Bromo-2-isopropyl-7-(4-methoxybenzylamino)-8-nitro-chromen-4-one (105 mg, 0.235 mmol), 4-chlorophenylboronic acid (73 mg, 0.47 mmol) and tetrakis(triphenylphosphine) palladium (0) (28 mg, 0.024 mmol) are dissolved in absolute ethanol (3 ml) in a 5 ml capacity microwave tube. Aqueous sodium carbonate solution (2M, 0.35 ml, 0.7 mmol) is added, and the mixture is heated at 100° C. under microwave irradiation for 10 min. The mixture is poured into water (10 ml) and extracted with ethyl acetate (3×30 ml). The ethyl acetate extracts are combined, washed with saturated brine (30 ml), dried ($MgSO_4$), filtered and evaporated to give a green solid. This is triturated with n-pentane and filtered to give a pale yellow powder.

7-Amino-3-(4-chlorophenyl)-2-isopropyl-8-nitro-chromen-4-one 3-(4-Chlorophenyl)-2-isopropyl-7-(4-methoxybenzylamino)-8-nitro-chromen-4-one (80 mg, 0.167 mmol) is dissolved in trifluoroacetic acid (2 ml), and the solution is stirred at room temperature for 2 h. The mixture is then poured onto crushed ice and warmed to room temperature, and the yellow precipitate formed is collected by filtration. The solid is washed with water and then dissolved in ethyl acetate (10 ml). The solution is washed sequentially with 50% aqueous sodium bicarbonate solution (10 ml) and saturated brine (10 ml), dried ($MgSO_4$), filtered and evaporated to give a pale yellow solid. This is triturated with n-pentane/diethyl ether and filtered to give a pale yellow powder.

7,8-Diamino-3-(4-chlorophenyl)-2-isopropyl-chromen-4-one

7-Amino-3-(4-chlorophenyl)-2-isopropyl-8-nitro-chromen-4-one (450 mg, 0.94 mmol) is suspended in methanol (5 ml). Concentrated hydrochloric acid (5 ml) is added. The mixture is placed under an atmosphere of argon, and 10% palladium on activated carbon (50 mg) is added. The reaction mixture is placed under an atmosphere of hydrogen and stirred at room temperature for 24 h. The mixture is filtered through a Celite pad, and the Celite pad is washed with methanol (3×30 ml). The filtrate and the washings are combined and evaporated to give a yellow solid.

7-(4-Chlorophenyl)-8-isopropyl-3H-chromeno[7,8-d]imidazol-6-one (and tautomer)

7,8-Diamino-3-(4-chlorophenyl)-2-isopropyl-chromen-4-one (43 mg, 0.13 mmol) is dissolved in formic acid (1.5 ml), and the solution is heated at reflux for 1 h. The reaction mixture is cooled to room temperature, diluted with ethyl acetate (40 ml) and washed with saturated sodium bicarbonate solution (2×30 ml), water (40 ml) and saturated brine (30 ml). The organic layer is dried ($MgSO_4$), filtered and evaporated to give a pale yellow solid. This is triturated with n-hexane/ethyl acetate/dichloromethane and filtered to give a colourless powder.

339.19, $(M+H)^+$. $^1$H NMR (400 MHz, DMSO-$d_6$): 13.2 (0.72H, br s, partially exchanged), 8.47 (1H, s), 7.85 (1H, d, J=8.6 Hz), 7.63 (1H, d, J=8.6 Hz), 7.53 (2H, m), 7.33 (2H, m), 2.87 (1H, m), 1.30 (6H, d, J=6.8 Hz). RT=3.918 min, purity=100%.

Example 6

7-(4-Chlorophenyl)-8-isopropyl-2-methyl-3H-chromeno[7,8-d]imidazol-6-one (and tautomer)

7,8-Diamino-3-(4-chlorophenyl)-2-isopropyl-chromen-4-one (80 mg, 0.243 mmol) is dissolved in glacial acetic acid (1.5 ml), dilute hydrochloric acid (2M, 0.1 ml) is added, and the mixture is heated at 120° C. for 90 min. The reaction mixture is cooled to room temperature, diluted with ethyl acetate (50 ml) and washed with saturated sodium bicarbonate solution (3×40 ml), water (40 ml) and saturated brine (40 ml). The organic layer is dried ($MgSO_4$), filtered and evaporated to give a brown solid. This is triturated with ethyl acetate containing a few drops of methanol and filtered to give a pale yellow powder.

353.25, $(M+H)^+$. $^1$H NMR (400 MHz, $CD_3OD$): 7.92 (1H, d, J=8.6 Hz), 7.52 (1H, d, J=8.6 Hz), 7.47 (2H, m), 7.28 (2H, m), 2.96 (1H, m), 2.68 (3H, s), 1.39 (6H, d, J=6.9 Hz). RT=3.427 min, purity >96%.

Example 7

7-(4-Chlorophenyl)-8-isopropyl-2-trifluoromethyl-3H-chromeno[7,8-d]imidazol-6-one (and tautomer)

7,8-Diamino-3-(4-chlorophenyl)-2-isopropyl-chromen-4-one (80 mg, 0.243 mmol) is dissolved in trifluoroacetic acid (1.4 ml), dilute hydrochloric acid (2M, 0.1 ml) is added, and the mixture is heated at 110° C. for 2.5 h. The reaction mixture is cooled to room temperature, diluted with ethyl acetate (50 ml) and washed with saturated sodium bicarbonate solution (2×40 ml), water (40 ml) and saturated brine (40 ml). The organic layer is dried ($MgSO_4$), filtered and evaporated to give a solid. This is triturated with dichloromethane containing a few drops of ethyl acetate and filtered to give a colourless powder.

407.29, $(M+H)^+$. $^1$H NMR (400 MHz, $CD_3OD$): 8.12 (1H, d, J=8.8 Hz), 7.69 (1H, d, J=8.8 Hz), 7.49 (2H, m), 7.31 (2H, m), 3.00 (1H, m), 1.41 (6H, d, J=6.9 Hz). RT=5.701 min, purity=100%.

Example 8

7-(4-Chlorophenyl)-2-(1,1-difluoroethyl)-8-isopropyl-3H-chromeno[7,8-d]imidazol-6-one (and tautomer)

7,8-Diamino-3-(4-chlorophenyl)-2-isopropyl-chromen-4-one (168 mg, 0.511 mmol) is dissolved in 2,2-difluoropropionic acid (562 mg), dilute hydrochloric acid (2M, 0.1 ml) is added, and the mixture is heated at 110° C. for 4 h. The reaction mixture is cooled to room temperature, diluted with water (10 ml) and extracted with ethyl acetate (3×30 ml). The ethyl acetate extracts are combined and washed with saturated sodium bicarbonate solution (2×40 ml) and saturated brine (40 ml). The organic layer is dried ($MgSO_4$), treated with decolourising charcoal (50 mg), filtered and evaporated to give a colourless solid. This is sonicated with n-hexane/diethyl ether and filtered to give a cream-coloured powder.

403, $(M+H)^+$. $^1$H NMR (400 MHz, DMSO-$d_6$): 14.5, 13.98 (0.9H, br s, partially exchanged), 7.94-7.5 (2H, br m), 7.51 (2H, m), 7.34 (2H, m), 2.88 (1H, m), 2.24 (3H, t, J=19.2 Hz), 1.30 (6H, br d). RT=5.45 min, purity >98%.

Example 9

2-(4-Chlorophenyl)-1-(2,4-dihydroxyphenyl)-ethanone

A mixture of resorcinol (100 g, 0.908 mol), 4-chlorophenylacetic acid (170 g, 0.999 mol) and boron trifluoride etherate is stirred mechanically at 85° C. for 1.75 h. The dark red-brown reaction mixture is allowed to cool to room temperature and then poured slowly into aqueous sodium acetate (1 l, 30% w/v). The suspension is stirred overnight at room temperature. The orange brown precipitate is removed by filtration, dried in vacuo and then triturated with isopropyl ether/hexane (1:9) to give a yellow solid. This solid is washed with hexane and dried in vacuo to provide the title compound. A further three crops of material are obtained from the sodium acetate work-up mixture.

3-(4-Chlorophenyl)-7-hydroxy-2-isopropyl-chromen-4-one

A mixture of 2-(4-chlorophenyl)-1-(2,4-dihydroxyphenyl)-ethanone (100 g, 0.382 mol), iso-butyric acid anhydride (380 ml, 2.29 mol) and dry pyridine (380 ml, 4.69 mol) is stirred at 140° C. for 12 h and then allowed to cool to room temperature. The volatile components are removed in vacuo, and the resulting dark brown oil is dried under high vacuum to give crude isobutyric acid 3-(4-chlorophenyl)-2-isopropyl-4-oxo-4H-chromen-7-yl ester. To a mixture of this crude ester and methanol (400 ml) is added aqueous KOH (250 ml, 5 M) [CAUTION: EXOTHERM]. The dark solution is stirred for 1.5 h, and the methanol is then evaporated in vacuo. The resulting solution is acidified with 2 M HCl to pH 3 to give a brown precipitate, which is removed by filtration. The brown solid is washed with water (3×) and isopropyl ether and then air-dried. The remaining aqueous solution is extracted with ethyl acetate (4×), and the combined organic phases are washed with water (3×), dried ($Na_2SO_4$) and evaporated to give a red oil, which solidifies to give a brown solid. The brown solid is washed with isopropyl ether and air-dried. The combined aqueous phases are extracted again (ethyl acetate) to provide a third crop of product.

3-(4-Chlorophenyl)-7-hydroxy-8-iodo-2-isopropyl-chromen-4-one 3-(4-Chlorophenyl)-7-hydroxy-2-isopropyl-chromen-4-one (2.3 g, 7.31 mmol) is suspended in dry dichloromethane (140 ml) at room temperature. N-iodosuccinimide (1.73 g, 7.67 mmol) is added, and the mixture is stirred vigorously at room temperature for 30 min. The mixture is diluted with dichloromethane (60 ml), washed with water (3×100 ml) and saturated brine (50 ml), dried (MgSO$_4$) and filtered, and the filtrate is evaporated to give a pale pink solid.

8-Acetyl-3-(4-chlorophenyl)-7-hydroxy-2-isopropyl-chromen-4-one 3-(4-Chlorophenyl)-7-hydroxy-8-iodo-2-isopropyl-chromen-4-one (1.1 g, 2.5 mmol), 1,3-bis(diphenylphosphino)propane (206 mg, 0.5 mmol), palladium acetate (56 mg, 0.25 mmol) and potassium carbonate (380 mg, 2.75 mmol) are mixed in N-methyl-2-pyrrolidinone (10 ml) in a 20 ml capacity microwave tube. Water (2 ml) and butyl vinyl ether (1.62 ml, 12.5 mmol) are added, the tube is sealed, and the mixture is heated at 80° C. under microwave irradiation for 45 min. The mixture is cooled to room temperature, poured into water (30 ml) and extracted with ethyl acetate (3×50 ml). The ethyl acetate extracts are combined, washed with saturated brine (50 ml), dried (MgSO$_4$), filtered and evaporated to give a brown solid. This is purified by chromatography on silica gel using cyclohexane/ethyl acetate (6:1) as eluant to give a colourless solid.

2,4,6-Trimethylbenzenesulfonic acid 8-acetyl-3-(4-chlorophenyl)-2-isopropyl-4-oxo-4H-chromen-7-yl ester 8-Acetyl-3-(4-chlorophenyl)-7-hydroxy-2-isopropyl-chromen-4-one (225 mg, 0.631 mmol) is dissolved in dry dichloromethane (6 ml) at room temperature. 2-(Mesitylene)sulfonyl chloride (237 mg, 1.08 mmol) and triethylamine (0.15 ml, 1.08 mmol) are added, and the mixture is stirred at room temperature for 16 h. Further quantities of 2-(mesitylene)sulfonyl chloride (166 mg, 0.757 mmol) and of triethylamine (0.106 ml, 0.757 mmol) are then added, and the mixture is stirred at room temperature for another 24 h. The mixture is then partitioned between ethyl acetate (50 ml) and water (50 ml) and extracted with additional portions of ethyl acetate (3×50 ml). The ethyl acetate extracts are combined, washed with saturated brine (50 ml), dried (MgSO$_4$), filtered and evaporated to give a colourless foam. This is purified by chromatography on silica gel using initially cyclohexane and then cyclohexane/ethyl acetate (1:1) as eluant to give a colourless solid.

3-(4-Chlorophenyl)-2-isopropyl-9-methyl-7H-pyrano[2,3-e]indazol-4-one 2,4,6-Trimethylbenzenesulfonic acid 8-acetyl-3-(4-chlorophenyl)-2-isopropyl-4oxo-4H-chromen-7-yl ester (470 mg, 0.87 mmol), ammonium acetate (339 mg, 4.4 mmol) and magnesium sulfate (530 mg, 4.4 mmol) are dissolved/suspended in toluene (7 ml) and ethanol (7 ml) in a 20 ml capacity microwave tube. Hydrazine hydrate (0.136 ml, 4.4 mmol) is added, the tube is sealed, and the mixture is heated at 140° C. under microwave irradiation for 2 h. The reaction mixture is then poured into water (20 ml) and extracted with ethyl acetate (3×20 ml). The ethyl acetate extracts are combined, washed with saturated brine (50 ml), dried (MgSO$_4$), filtered and evaporated to give a light brown solid. This is absorbed onto silica gel and purified by chromatography on silica gel using n-hexane/ethyl acetate (0-50% ethyl acetate) as eluant to give the product as a colourless solid.

353, (M+H)$^+$. $^1$H NMR (400 MHz, CDCl$_3$): 8.13 (1H, d, J=8.8 Hz), 7.41 (2H, m), 7.34 (1H, d, J=8.8 Hz), 7.23 (2H, m), 3.02 (1H, m), 2.88 (3H, s), 1.35 (6H, d, J=6.9 Hz). RT=5.25 min, purity=98.5%.

Example 10

3-(4-Chlorophenyl)-7-hydroxy-2-isopropyl-4-oxo-4H-chromene-8-carbaldehyde

A mixture of 3-(4-chlorophenyl)-7-hydroxy-2-isopropyl-chromen-4-one (12.48 g, 39.6 mmol) and hexamethylenetetramine (39.46 g, 0.28 mol) in acetic acid (250 ml) is stirred at 100° C. for 20 h. After the mixture has cooled to room temperature, the solvent is removed in vacuo to afford a black oily residue. 5M HCl solution (150 ml) is added, and the mixture is heated under reflux for 30 min. The reaction mixture is poured onto ice/water, and the resulting brown solid is isolated by filtration. The solid is taken up in dichloromethane, the mixture is passed through a bed of Celite, and the solvent is evaporated in vacuo. The solid residue is stirred at room temperature with ethyl acetate, filtered and washed with hexane to afford the desired product as a pale brown solid.

2,4,6-Trimethylbenzenesulfonic acid 3-(4-chlorophenyl)-8-formyl-2-isopropyl-4-oxo-4H-chromen-7-yl ester To a solution of 3-(4-chlorophenyl)-7-hydroxy-2-isopropyl-4-oxo-4H-chromene-8-carbaldehyde (2.19 g, 6.39 mmol) in dry dichloromethane (55 ml) at room temperature are added triethylamine (0.926 ml, 6.64 mmol), 2-(mesitylene)sulfonyl chloride (1.46 g, 6.65 mmol) and 4-dimethylaminopyridine (50 mg, catalytic amount). The mixture is stirred at room temperature for 20 h and then quenched by the addition of saturated sodium bicarbonate solution (60 ml). The organic phase is separated, and the aqueous phase is extracted with dichloromethane (2×40 ml). The organic phases are combined, washed with saturated brine (50 ml), dried (MgSO$_4$), filtered and evaporated under reduced pressure. The residue is purified by chromatography on silica gel using 10% ethyl acetate in cyclohexane as eluant to give the product as a colourless solid.

3-(4-Chlorophenyl)-2-isopropyl-7H-pyrano[2,3-e]indazol-4-one

To a suspension of 2,4,6-trimethylbenzenesulfonic acid 3-(4-chlorophenyl)-8-formyl-2-isopropyl-4-oxo-4H-chromen-7-yl ester (391 mg, 0.745 mmol), magnesium sulphate (450 mg, 3.72 mmol) and ammonium acetate (230 mg, 2.98 mmol) in ethanol (15 ml) in a 20 ml microwave tube is added hydrazine hydrate (0.93 ml, 2.98 mmol). The tube is sealed and heated at 145° C. for ca. 80 min. The mixture is cooled to room temperature, and the volatiles are evaporated under reduced pressure. The residue is dissolved in dry pyridine (14 ml), the solution is transferred to a 20 ml microwave tube, the tube is sealed, and the mixture is heated at 190° C. for 100 min. The mixture is cooled and evaporated to dryness. The residue is purified by chromatography on silica gel using cyclohexane/ethyl acetate (6:1) as eluant.

339.21, (M+H)+. 1H NMR (400 MHz, CDCl3): 8.42 (1H, s), 8.19 (1H, d, J=8.8 Hz), 7.44 (3H, m), 7.26 (1H, m), 3.01 (1H, m), 1.35 (6H, d, J=6.2 Hz). RT=5.082 min, purity=100%.

Example 11

3-(4-Chlorophenyl)-9-iodo-2-isopropyl-7H-pyrano [2,3-e]indazol-4-one

To a solution of 3-(4-chlorophenyl)-2-isopropyl-7H-pyrano[2,3-e]indazol-4-one (20 mg, 0.059 mmol) in dry N,N-dimethylformamide (2 ml) at room temperature are added potassium hydroxide (6.3 mg, 0.112 mmol) and iodine (55 mg, in three portions over 3 h, 0.217 mmol). The reaction mixture is stirred at room temperature for 20 h, then diluted with ethyl acetate and washed successively with 10% aqueous sodium thiosulfate solution (40 ml) and saturated brine (40 ml). The organic phase is dried (MgSO4), filtered and evaporated under reduced pressure. The resulting solid is triturated with n-hexane/dichloromethane to give a colourless solid that is recovered by filtration and dried.

465.19, (M+H)+. 1H NMR (400 MHz, DMSO-d6): 14.1 (1H, br s), 7.95 (1H, d, J=8.9 Hz), 7.60 (1H, d, J=8.9 Hz), 7.52 (2H, m), 7.33 (2H, m), 2.93 (1H, m), 1.42 (6H, d, J=6.8 Hz). RT=6.006 min, purity=100%.

Example 12

7-(4-Chlorophenyl)-8-isopropyl-3H-9-oxa-1,2,3-triaza-cyclopenta[a]naphthalen-6-one (and tautomer)

A stirred mixture of 7,8-diamino-3-(4-chlorophenyl)-2-isopropyl-chromen-4-one (115 mg, 0.35 mmol) and 5% aqueous acetic acid (5 ml) is cooled to 0° C., and sodium nitrite (26 mg, 0.38 mmol) is added portionwise. The mixture is stirred for 18 h as it is allowed to warm to room temperature. The reaction is quenched with saturated aqueous sodium bicarbonate (50 ml), and the mixture is extracted with ethyl acetate (3×50 ml). The organic phases are combined, washed with saturated aqueous sodium bicarbonate (50 ml) and then with saturated brine (50 ml), dried (MgSO4), filtered and evaporated under reduced pressure. The residue is purified by chromatography on silica gel using n-hexane/ethyl acetate (0-100% ethyl acetate) as eluant to give the product as a colourless solid.

340.16, (M+H)+. 1H NMR (400 MHz, DMSO-d6): 8.02 (1H, d, J=8.8 Hz), 7.85 (1H, d, J=8.8 Hz), 7.55 (2H, m), 7.36 (2H, m), 2.89 (1H, m), 1.32 (6H, d, J=6.8 Hz). RT=4.671 min, purity=100%.

Example 13

3-(4-Chlorophenyl)-2-isopropyl-8,9,10,11-tetrahydro-7H-1-oxa-7,10-diaza-cyclohepta[a]naphthalen-4-one A mixture of 2,4,6-trimethylbenzenesulfonic acid 3-(4-chlorophenyl)-8-formyl-2-isopropyl-4-oxo-4H-chromen-7-yl ester (141 mg, 0.269 mmol) and ethylene diamine (0.6 ml) in anhydrous pyridine (3.5 ml) in a sealed 5 ml microwave tube is heated under microwave irradiation at 100° C. for 1 h. A further aliquot of ethylene diamine (0.6 ml) is added, and the mixture is heated at 140° C. for 30 min. A further aliquot of ethylene diamine (0.4 ml) is then added, and the mixture is heated at 160° C. for 50 min and finally at 150° C. for 2 h. The mixture is cooled to room temperature, and the volatiles are removed under reduced pressure. The residue is dissolved in dry methanol (4 ml), and the solution is cooled to 0° C. Sodium borohydride (15 mg, 0.4 mmol) is added, and the mixture is stirred for 18 h as it warms to room temperature. The mixture is quenched by the addition of water (30 ml) and extracted with dichloromethane (3×20 ml). The organic phases are combined, washed with saturated brine (50 ml), dried (MgSO4), filtered and evaporated under reduced pressure. The residue is purified by preparative reversed phase chromatography using 90% water/-acetonitrile to 100% acetonitrile as eluant. The pure product-containing fractions are combined and evaporated to dryness, and the residue is triturated with n-hexane containing a small amount of dichloromethane. The resulting colourless powder is recovered by filtration and dried.

369.27, (M+H)+. 1H NMR (400 MHz, CDCl3): 8.01 (1H, d, J=8.8 Hz), 7.39 (2H, m), 7.20 (2H, m), 6.94 (1H, d, J=8.8 Hz), 5.90 (1H, brs), 3.91 (1H, brs), 3.55-3.25 (5H, m), 3.15 (1H, m), 2.95 (1H, m), 1.32 (6H, br d). RT=2.233 min, purity=100%.

Example 14

4-(6-Isopropyl-8-oxo-1,2,3,8-tetrahydro-4,5-dioxa-1-aza-phenanthren-7-yl)benzonitrile A mixture of 7-(4-chlorophenyl)-6-isopropyl-2,3-dihydro-1H-1-aza-4,5-dioxa-phenanthren-8-one (71.7 mg, 0.202 mmol), tris(dibenzylideneacetone)dipalladium (0) (92.2 mg, 0.101 mmol), 1,1'-bis(diphenylphosphino)ferrocene (112 mg, 0.202 mmol) and zinc cyanide (24 mg, 0.204 mmol) in N,N-dimethylformamide (2.5 ml) is heated at 180° C. for 40 min under microwave irradiation in an Emrys Optimizer instrument (Biotage AB, Uppsala, Sweden). The mixture is filtered through a short pad of Celite, which is then thoroughly washed through with ethyl acetate. The filtrate is washed successively with water and brine. The organic layer is dried (MgSO4) and concentrated in vacuo. The residue is purified by flash chromatography (cyclohexane/ethyl acetate gradient) to afford the title compound.

347.32, (M+H)+. 1H NMR (400 MHz, DMSO-d6): 7.90 (2H, d, J=8.29 Hz), 7.46 (2H, d, J=8.29 Hz), 7.37 (1H, d, J=8.67 Hz), 6.90 (1H, br s), 6.70 (1H, d, J=8.69 Hz), 4.28-4.26 (2H, m), 3.30 (2H, br s), 2.73-2.69 (1H, m), 1.16 (6H, d, J=6.91 Hz). RT=4.480 min, purity=100%.

Example 15

7-(4-Chlorophenyl)-6-isopropyl-1H-4,5-dioxa-1-aza-phenanthrene-2,8-dione 2-(4-Chlorophenyl)-1-(4-fluoro-2-hydroxy-phenyl)-ethanone To a solution of 4-chlorophenylacetyl chloride (27.6 g, 0.15 mol) in 1,2-dichloroethane (200 ml), cooled to 0° C. in an ice bath, under nitrogen is added slowly AlCl3 (21.8 g, 0.16 mol). The reaction mixture is stirred at 0° C. for 20 min. 3-fluorophenol (12.2 g, 0.11 mol) is added, and the reaction mixture is allowed to warm to room temperature, then heated at 90° C. for 16 h. The reaction mixture is cooled to room temperature, then poured cautiously into aqueous ammonia solution (500 ml) with vigourous stirring. The mixture is diluted with CH2Cl2 (250 ml) and filtered through Celite. The organic phase is separated, washed with water, brine and dried (MgSO4). The solvent is removed in vacuo, and the crude product is purified by flash chromatography on silica gel using iso-hexane:ethyl acetate (10:1 to 4:1) as the eluent to give the title compound.

[M+H]+ 265.

Isobutyric acid 2-[2-(4-chlorophenyl)-acetyl]-5-fluoro-phenyl ester

To a solution of 2-(4-chlorophenyl)-1-(4-fluoro-2-hydroxy-phenyl)-ethanone (16.0 g, 60.6 mmol) in $CH_2Cl_2$ (300 ml) is added triethylamine (7.4 g, 72.7 mmol). A solution of isobutyryl chloride (7.1 g, 66.6 mmol) in $CH_2Cl_2$ (100 ml) is added slowly over 30 min. The reaction mixture is stirred at room temperature for 2 h. The organic phase is washed with 0.5 M HCl, water and brine and dried ($MgSO_4$). The solvent is removed in vacuo, and the product is purified by flash chromatography on silica gel using iso-hexane:ethyl acetate (20:1 to 10:1) as the eluent to give the title compound.

$^1$H-NMR (400 MHz, $CDCl_3$): 7.80 (1H, m), 7.32 (2H, d), 7.16 (2H, d), 7.03 (1H, m), 6.88 (1H, m), 4.17 (2H, s), 2.83 (1H, m), 1.33 (6H, d).

2-(4-Chlorophenyl)-1-(4-fluoro-2-hydroxy-phenyl)-4-methyl-pentane-1,3-dione

To a solution of isobutyric acid 2-[2-(4-chlorophenyl)-acetyl]-5-fluoro-phenyl ester (16.4 g, 49.0 mmol) in dry THF (250 ml) under an argon atmosphere is added portionwise NaH (9.8 g, 254 mmol) at room temperature. The reaction mixture is heated at 80° C. for 2 h, cooled to room temperature and then poured carefully into ice-water containing 10% $NH_4Cl$ (300 ml).

Ethyl acetate (250 ml) is added with stirring, and the layers are separated. The aqueous phase is washed with further ethyl acetate (200 ml), and the organic phases are combined, washed with water and brine and dried ($MgSO_4$). The solvent is removed in vacuo to afford the title compound.

3-(4-Chloro-phenyl)-7-fluoro-2-isopropyl-chromen-4-one

To a solution of 2-(4-chlorophenyl)-1-(4-fluoro-2-hydroxy-phenyl)-4-methyl-pentane-1,3-dione (16.4 g, 49 mmol) in glacial acetic acid (150 ml) is added concentrated HCl (20 ml). The reaction mixture is stirred at 140° C. for 2 h, allowed to cool and then poured into a mixture of 880 ml of ammonium hydroxide and ice (200 ml). Ethyl acetate (300 ml) is added with vigorous stirring. The phases are separated, and the aqueous phase is washed with ethyl acetate (200 ml). The organic phases are combined, washed with water and brine and dried ($MgSO_4$). The solvent is removed in vacuo, and the crude product is purified by flash chromatography on silica gel using iso-hexane:ethyl acetate (25:1 to 15:1) as the eluent. The resulting oil is crystallised from iso-hexane (150 ml) to give the title compound.

[M+H] 317.

7-Azido-3-(4-chlorophenyl)-2-isopropyl-chromen-4-one

To a solution of 3-(4-chlorophenyl)-7-fluoro-2-isopropyl-chromen-4-one (4.0 g, 12.7 mmol) in dry dimethylformamide (120 ml) is added sodium azide at room temperature. The reaction mixture is heated at 90° C. for 16 h, cooled to room temperature and partitioned between ethyl acetate and water. The organic phase is washed with water and brine, dried ($MgSO_4$) and concentrated in vacuo. Purification by flash chromatography on silica gel using iso-hexane:ethyl acetate (10:1) as the eluent, followed by recrystallisation from iso-hexane, gives the title compound.

[M+H]+ 340.

7-(4-Chlorophenyl)-8-isopropyl-2-methyl-chromeno[7,8-d]oxazol-6-one

Acetic acid (20 ml) is added to polyphosphoric acid (~25 g) heated to 80° C. The viscous solution is stirred vigorously for 5 min. 7-azido-3-(4-chlorophenyl)-2-isopropyl-chromen-4-one (1.0 g, 2.95 mmol) is added portionwise over a period of 10 min. The reaction mixture is heated at 120° C. for 3 h, cooled to room temperature and poured into water (200 ml), and the product is extracted with $CH_2Cl_2$. The organic phase is washed with water and brine, dried ($MgSO_4$) and filtered. Methanol (30 ml) is added, followed by partial evaporation in vacuo to give a precipitate, which is isolated by filtration.

[M+H]+ 354.

7-Amino-3-(4-chlorophenyl)-8-hydroxy-2-isopropyl-chromen-4-one

To a suspension of 7-(4-chlorophenyl)-8-isopropyl-2-methyl-chromeno[7,8-d]oxazol-6-one (650 mg, 1.84 mmol) in methanol (30 ml) is added concentrated HCl (5 ml). The reaction mixture is stirred at 70° C. for 1 h. The solvent is removed in vacuo, and the product is partitioned between $CH_2Cl_2$ and a saturated solution of $NaHCO_3$. The organic phase is washed with water and brine, dried ($MgSO_4$) and concentrated in vacuo to give the title compound as a pale yellow solid.

[M+H]+ 330.

7-(4-Chlorophenyl)-6-isopropyl-1H-4,5-dioxa-1-aza-phenanthrene-2,8-dione

A mixture of 7-amino-3-(4-chlorophenyl)-8-hydroxy-2-isopropyl-chromen-4-one (250 mg, 0.75 mmol), $CDCl_3$ (1 ml), saturated $NaHCO_3$ solution (1.5 ml) and bromoacetyl-bromide (169 mg, 0.85 mmol) is stirred vigorously at room temperature for 5 min and then passed through an Isolute™ phase separator to separate the organic phase, which is then treated with dimethylformamide (1 ml) and $K_2CO_3$ (115 mg, 0.85 mmol) and heated in a microwave at 90° C. for 15 min. The reaction mixture is partitioned between $CH_2Cl_2$ and water. The organic phase is washed with water and brine, dried ($MgSO_4$) and concentrated in vacuo, followed by crystallisation from methanol. The product is partitioned between ethyl acetate and water to remove traces of dimethylformamide. The organic phase is dried ($MgSO_4$), concentrated in vacuo and crystallised from methanol to yield the title compound.

[M+H]+ 370. $^1$H-NMR (DMSO-$d_6$, 400 MHz) 11.20 (1H, s), 7.60 (1H, d), 7.50 (2H, d), 7.30 (2H, d), 7.00 (1H, d), 4.82 (2H, s), 2.80 (1H, m), 1.20 (6H, d).

Example 16

Preparation of Soft Gelatin Capsules

5'000 soft gelatin capsules, each comprising as active ingredient 0.05 g of one of the agents of the invention, are prepared as follows:

Composition
Active ingredient 250 g
Lauroglycol® 2 l

The pulverized active ingredient is suspended in Lauroglykol® (propylene glycol laurate, Gattefossé S.A., Saint Priest, France) and ground in a wet pulverizer to produce a particle size of about 1-3 μm. 0.419 g portions of the mixture are then introduced into soft gelatin capsules using a capsule-filling machine.

The invention claimed is:

1. A compound of the formula

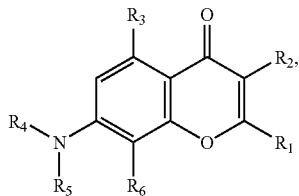

(I)

in which

R$_1$ is halogen or C$_1$-C$_8$alky phenyl substituted with 1, 2 or 3 substituents each independently selected from halogen or cyano;

R$_3$ is hydrogen;

R$_4$ is hydrogen, or formyl; and

N—R$_5$ and R$_6$, taken together, are a moiety N—X—O (lbb), in which —X—is —C(=O)—or —(CH$_2$,)$_a$—, in which a is 2 or 3 and in which any methylene group, independently from any other methylene group in the moiety lbb, is, optionally, mono-substituted by oxo or substituted by 1 or 2 substituents, selected from the group consisting of C$_1$-C$_6$alkyl and hydroxy-C$_1$-C$_6$alkyl, or N—R$_5$ and R$_6$—, taken together, are a moiety N—C(R$_a$)=C(R$_b$)— (ldd), in which R$_a$ is hydrogen and R$_b$ is C$_1$-C$_6$alkyl, or N—R$_5$ and R$_6$—, taken together, are a moiety N—C(R$_c$)=N— (lee), in which R$_c$ is hydrogen, C$_1$-C$_6$alkyl or halo-C$_1$-C$_6$alkyl, or N—R$_5$ and R$_6$—, taken together, are a moiety N—N=C (R$_d$)— (lff), in which R$_d$ is hydrogen or C$_1$-C$_6$alkyl, or N—R$_5$, and R$_6$—, taken together, are a moiety N—N=C(R$_1$)— (Ig), in which R$_1$ is halogen, or N—R$_5$ and R$_6$—, taken together, are a moiety N=N—N— (Ih) or N—R$_5$ and R$_6$—, taken together, are a moiety N—(CH$_2$,)$_2$—N(H)—C(R$_g$)H— (Iii), in which R$_g$ is hydrogen;

in free form or in salt form.

2. A method for treating nociceptive pain comprising:
administering to a mammal in need thereof a therapeutically effective amount of the compound as defined in claim 1 of the formula I, in free form or in pharmaceutically acceptable salt form.

3. A pharmaceutical compositions comprising:
the compound as defined in claim 1 of the formula I, in free form or in pharmaceutically acceptable salt form, in association with a pharmaceutical carrier or diluent.

4. A combination comprising a therapeutically effective amount of a compound as defined in claim 1 of the formula I, in free form or in pharmaceutically acceptable salt form, and a second drug substance, for simultaneous or sequential administration.

* * * * *